US009897916B2

(12) United States Patent
Ohashi et al.

(10) Patent No.: US 9,897,916 B2
(45) Date of Patent: Feb. 20, 2018

(54) COMPOUND, POLYMER COMPOUND, RESIST COMPOSITION, AND PATTERNING PROCESS

(71) Applicant: SHIN-ETSU CHEMICAL CO., LTD., Tokyo (JP)

(72) Inventors: Masaki Ohashi, Jyoetsu (JP); Jun Hatakeyama, Jyoetsu (JP); Masahiro Fukushima, Jyoetsu (JP); Takayuki Fujiwara, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/195,395

(22) Filed: Jun. 28, 2016

(65) Prior Publication Data
US 2017/0038683 A1 Feb. 9, 2017

(30) Foreign Application Priority Data

Aug. 5, 2015 (JP) ................................. 2015-155343

(51) Int. Cl.
| | | |
|---|---|---|
| *G03F 7/039* | (2006.01) | |
| *G03F 7/38* | (2006.01) | |
| *C07C 309/12* | (2006.01) | |
| *C07D 327/08* | (2006.01) | |
| *C08F 220/20* | (2006.01) | |
| *C08F 220/32* | (2006.01) | |
| *G03F 7/038* | (2006.01) | |
| *G03F 7/16* | (2006.01) | |
| *G03F 7/20* | (2006.01) | |
| *G03F 7/32* | (2006.01) | |
| *C08F 220/38* | (2006.01) | |
| *C08F 220/18* | (2006.01) | |
| *C08F 220/28* | (2006.01) | |
| *C08F 220/30* | (2006.01) | |

(52) U.S. Cl.
CPC ............ *G03F 7/039* (2013.01); *C07C 309/12* (2013.01); *C07D 327/08* (2013.01); *C08F 220/38* (2013.01); *G03F 7/038* (2013.01); *G03F 7/168* (2013.01); *G03F 7/2004* (2013.01); *G03F 7/2041* (2013.01); *G03F 7/322* (2013.01); *G03F 7/38* (2013.01); *C07C 2601/14* (2017.05); *C07C 2602/42* (2017.05); *C07C 2603/74* (2017.05); *C08F 220/20* (2013.01); *C08F 2220/1891* (2013.01); *C08F 2220/283* (2013.01); *C08F 2220/302* (2013.01); *C08F 2220/303* (2013.01); *C08F 2220/382* (2013.01)

(58) Field of Classification Search
None
See application file for complete search history.

(56) References Cited

U.S. PATENT DOCUMENTS

| | | | | |
|---|---|---|---|---|
| 5,945,250 A | * | 8/1999 | Aoai ..................... | G03F 7/0045 430/270.1 |
| 7,455,952 B2 | * | 11/2008 | Hatakeyama ......... | G03F 7/2041 430/270.1 |
| 8,691,490 B2 | * | 4/2014 | Ohashi .................... | C07C 69/54 430/270.1 |
| 8,900,793 B2 | * | 12/2014 | Sagehashi ............. | G03F 7/0045 430/270.1 |
| 2003/0013039 A1 | | 1/2003 | Kobayashi et al. | |
| 2006/0228648 A1 | | 10/2006 | Ohsawa et al. | |
| 2008/0090172 A1 | | 4/2008 | Hatakeyama et al. | |
| 2008/0102407 A1 | | 5/2008 | Ohsawa et al. | |
| 2008/0118860 A1 | | 5/2008 | Harada et al. | |
| 2008/0187860 A1 | | 8/2008 | Tsubaki et al. | |

(Continued)

FOREIGN PATENT DOCUMENTS

| | | |
|---|---|---|
| CA | 2049772 A1 | 2/1992 |
| JP | H04-230645 A | 8/1992 |

(Continued)

OTHER PUBLICATIONS

Machine translation of JP 2011-150211 (2011).*

(Continued)

*Primary Examiner* — Martin Angebranndt
(74) *Attorney, Agent, or Firm* — Oliff PLC

(57) ABSTRACT

The present invention provides a compound shown by the formula (1),

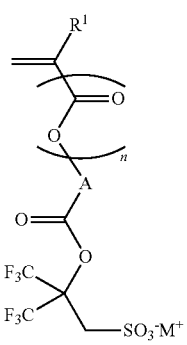

wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; "n" represents 0 or 1, provided that "n" is 0 when A is a single bond; and $M^+$ represents a cation. This compound is suitable as a raw material of a polymer compound usable for a base resin of a resist composition that has high resolution and high sensitivity and is excellent in balance of lithography properties such as LWR and CDU.

11 Claims, 4 Drawing Sheets

(56) References Cited

U.S. PATENT DOCUMENTS

| | | |
|---|---|---|
| 2009/0011366 A1 | 1/2009 | Tsubaki et al. |
| 2009/0081588 A1 | 3/2009 | Hatakeyama et al. |
| 2009/0111047 A1 | 4/2009 | Yamashita |
| 2009/0208867 A1 | 8/2009 | Harada et al. |
| 2009/0208873 A1 | 8/2009 | Harada et al. |
| 2009/0280434 A1 | 11/2009 | Harada et al. |
| 2009/0318652 A1 | 12/2009 | Nagai et al. |
| 2010/0055608 A1 | 3/2010 | Ohashi et al. |
| 2010/0099042 A1 | 4/2010 | Ohashi et al. |
| 2010/0112482 A1 | 5/2010 | Watanabe et al. |
| 2010/0136482 A1 | 6/2010 | Harada et al. |
| 2010/0143830 A1 | 6/2010 | Ohashi et al. |
| 2010/0183975 A1 | 7/2010 | Takahashi et al. |
| 2010/0209827 A1 | 8/2010 | Ohashi et al. |
| 2010/0248149 A1* | 9/2010 | Tsuchimura ........... C08F 224/00 430/296 |
| 2010/0266957 A1 | 10/2010 | Harada et al. |
| 2011/0183263 A1* | 7/2011 | Takahashi ............. G03F 7/0045 430/270.1 |
| 2012/0045724 A1 | 2/2012 | Ohsawa et al. |
| 2012/0065291 A1* | 3/2012 | Matsumura ........... G03F 7/0045 522/183 |
| 2012/0100486 A1 | 4/2012 | Sagehashi et al. |
| 2013/0005997 A1* | 1/2013 | Sagehashi ............ C07D 301/24 549/518 |
| 2013/0065182 A1* | 3/2013 | Mori ...................... C07C 309/10 430/285.1 |
| 2013/0101936 A1* | 4/2013 | Taniguchi ............. G03F 7/0045 430/280.1 |
| 2013/0224657 A1 | 8/2013 | Ohashi et al. |
| 2013/0337378 A1 | 12/2013 | Ohashi et al. |
| 2014/0272707 A1 | 9/2014 | Fukushima et al. |
| 2014/0322650 A1 | 10/2014 | Ohashi et al. |

FOREIGN PATENT DOCUMENTS

| | | | |
|---|---|---|---|
| JP | 09-005994 | * | 1/1997 |
| JP | 2003-066612 A | | 3/2003 |
| JP | 2005-084365 A | | 3/2005 |
| JP | 2007-145797 A | | 6/2007 |
| JP | 2008-111103 A | | 5/2008 |
| JP | 2008-122932 A | | 5/2008 |
| JP | 2008-133448 A | | 6/2008 |
| JP | 2008-281974 A | | 11/2008 |
| JP | 2008-281975 A | | 11/2008 |
| JP | 2009-098638 A | | 5/2009 |
| JP | 2009-109595 A | | 5/2009 |
| JP | 2009-191151 A | | 8/2009 |
| JP | 2009-192784 A | | 8/2009 |
| JP | 2009-276363 A | | 11/2009 |
| JP | 2010-077404 A | | 4/2010 |
| JP | 2010-107695 A | | 5/2010 |
| JP | 2010-116550 A | | 5/2010 |
| JP | 2010-134012 A | | 6/2010 |
| JP | 2010-155824 A | | 7/2010 |
| JP | 2010-164963 A | | 7/2010 |
| JP | 2010-215608 A | | 9/2010 |
| JP | 4554665 B2 | | 9/2010 |
| JP | 2010-250105 A | | 11/2010 |
| JP | 2011-042789 A | | 3/2011 |
| JP | 2007-238060 | * | 7/2011 |
| JP | 2007-328060 | * | 7/2011 |
| JP | 2011-150211 | * | 8/2011 |
| JP | 2012-041320 A | | 3/2012 |
| JP | 2012-046501 A | | 3/2012 |
| JP | 2012-106986 A | | 6/2012 |
| JP | 2013-209360 A | | 10/2013 |
| JP | 2014-001259 A | | 1/2014 |
| JP | 2014-177407 A | | 9/2014 |
| JP | 2014-225005 A | | 12/2014 |
| WO | 2007/069640 A | | 6/2007 |
| WO | 2009/019793 | * | 12/2009 |

OTHER PUBLICATIONS

Dammel et al, 193 nm Immersion Lithograpyhy—Taking the Plunge, "Journal of Photopolymer Science and Technology," vol. 17, No. 4, pp. 587-602, May 19, 2004.

* cited by examiner

COMPOUND, POLYMER COMPOUND, RESIST COMPOSITION, AND PATTERNING PROCESS

BACKGROUND OF THE INVENTION

Field of the Invention

The present invention relates to a compound having a structure that functions as a photo acid generator, a polymer compound having a repeating unit that functions as a photo acid generator, a resist composition containing the polymer compound, and a patterning process using the resist composition.

Description of the Related Art

A finer pattern rule has been recently required for Large-Scale Integrated circuits (LSI) with higher integration and higher processing speed. Under such circumstances, a far ultraviolet lithography and a vacuum ultraviolet lithography are promising for the next generation fine patterning technologies. Especially, a photolithography using an ArF excimer laser beam as a light source (an ArF lithography) is an indispensable technology for an ultrafine patterning process with a size of 0.13 µm or less.

The ArF lithography started to be used partially from production of 130-nm node devices, and then it has been used as a main lithography technology from production of 90-nm node devices. As a lithography technology for the next 45-nm node devices, a 157-nm lithography using $F_2$ laser was initially considered as a promising technology. However, a delay in development thereof due to several problems was indicated. Then, an ArF immersion lithography rapidly emerged and is now in the stage of practical use. In the ArF immersion lithography, a liquid whose refractive index is higher than air, such as water, ethylene glycol, and glycerin, is placed between a projection lens and a wafer. This enables the number of aperture (NA) of the projection lens to be 1.0 or more, thereby attaining high resolution (for example, see Non-Patent Document 1). For this immersion lithography, a resist composition not readily eluting into water is required.

The ArF lithography requires a highly sensitive resist composition that can express a sufficient resolution with a small exposure dose to prevent degradation of a precise and expensive optical material. To obtain the highly sensitive resist composition, components having high transparency at a wavelength of 193 nm are usually selected as the components contained in the resist composition. For example, polyacrylic acid, derivatives thereof, norbornene-maleic anhydride alternating copolymer, polynorbornene, ring-opening metathesis polymers, and hydrogenated ring-opening metathesis polymers have been proposed as the base resin. These compounds bring a certain level of results in enhancing transparency of the resin alone.

In addition, a negative tone development with an organic solvent has recently attracted attention, as well as a positive tone development with an alkaline developer. The negative tone development can form an ultrafine hole pattern, which is not achievable by the positive tone development, by organic solvent development that uses a positive resist composition having high resolution. Moreover, an attempt to double the resolution by combining two developments of the alkaline development and the organic solvent development is under study.

As an ArF resist composition for the negative tone development with an organic solvent, conventional positive ArF resist compositions can be used. Patent Documents 1 to 3 disclose patterning processes using the conventional positive ArF resist compositions.

The resist compositions have developed with the rapid trend towards miniaturization in recent years, as well as the process technology, and various photo-sensitive acid generators have been studied. As the photo acid generator, sulfonium salts of triphenylsulfonium cation and perfluoroalkane sulfonate anion are commonly used. Unfortunately, these salts generate perfluoroalkanesulfonic acid, especially perfluorooctane sulfonic acid (PFOS), which has low decomposability, biological concentration, and toxicity, and thus are difficult to be used for the resist composition. Then, a photo acid generator that generates perfluorobutane sulfonic acid is currently used. However, when the photo acid generator that generates perfluorobutane sulfonic acid is used for the resist composition, a generated acid considerably diffuses, and thus high resolution is difficult to be achieved. To solve this problem, various alkanesulfonic acids partially substituted with fluorine and salts thereof are studied. For example, Patent Document 1 mentions, as the prior art, a photo acid generator that generates α,α-difluoroalkanesulfonic acid by exposure, more specifically a photo acid generator that generates di(4-tert-butylphenyl)iodonium-1,1-difluoro-2-(1-naphthyl)ethanesulfonate or an α,α,β,β-tetrafluoroalkanesulfonic acid. Although these generators are substituted with less fluorine, they contain no decomposable substituent such as an ester structure and thus are insufficient in view of environmental safety due to easily decomposability. Furthermore, there are other problems of limitation in the molecular design to change the size of the alkanesulfonic acid and cost of fluorine-containing starting materials.

Patent Document 4 discloses a photo acid generator having 2-acyloxy-1,1,3,3,3-pentafluoropropane-1-sulfonic acid. This generator has easily decomposability and advantageously environmental safety, and allows various design by changing an acyl group. In particular, introduction of a bulky substituent or a poplar group into the photo acid generator is effective in controlling acid diffusion. For example, a photo acid generator having 2-(1-adamantyloxy)-1,1,3,3,3-pentafluoropropane-1-sulfonic acid can reduce the acid diffusion to some extent. However, the resist composition disclosed in Patent Document 4 becomes unsatisfactory as the acid diffusion increases and affects lithography properties with a recent decrease in circuit line width. In particular, line width roughness (LWR) and critical dimension uniformity (CDU) significantly deteriorate by the effect of acid diffusion.

In this context, many attempts are made to incorporate a repeating unit that functions as a photo acid generator into the base resin so as to control the acid diffusion. For example, Patent Document 5 discloses a polymer compound obtained by polymerizing an acryloyloxyphenyldiphenyl sulfonium salt, and Patent Document 6 discloses polymerizing and thereby incorporating the acryloyloxyphenyldiphenyl sulfonium salt into the base resin to improve LWR of a polyhydroxystyrene resin. In these resins, however, the cation side bonds to the polymer compound, so that a sulfonic acid generated therefrom by irradiation with a high energy beam is similar to a sulfonic acid generated from the conventional photo acid generator. Thus, such resins are insufficient for controlling the acid diffusion. On the other hand, Patent Documents 7 and 8 disclose a polymer obtained by polymerizing a sulfonium salt and a resist composition containing a polymer whose skeleton is fluorinated, which improve LWR to some extent. However, these materials are still insufficient in lithography properties such as LWR, considering the trend towards miniaturization and finer patterning for the next 32-nm node and later one.

PRIOR ART DOCUMENTS

Patent Documents

Patent Document 1: Japanese Patent Laid-Open Publication No. 2008-281974
Patent Document 2: Japanese Patent Laid-Open Publication No. 2008-281975
Patent Document 3: Japanese Patent No. 4554665
Patent Document 4: Japanese Patent Laid-Open Publication No. 2007-145797
Patent Document 5: Japanese Patent Laid-Open Publication No. H04-230645
Patent Document 6: Japanese Patent Laid-Open Publication No. 2005-84365
Patent Document 7: Japanese Patent Laid-Open Publication No. 2010-116550
Patent Document 8: Japanese Patent Laid-Open Publication No. 2010-077404

Non-Patent Documents

Non-Patent Document 1: Journal of photopolymer Science and Technology Vol. 17, No. 4, p 587 (2004)

SUMMARY OF THE INVENTION

The present invention has been accomplished under the above circumstances, and an object thereof is to provide a resist composition capable of forming a resist film that has high resolution and high sensitivity and is excellent in balance of lithography properties such as LWR and CDU; a polymer compound suitable as a base resin of the resist composition; a compound suitable as a raw material of the polymer compound; and a patterning process using the resist composition.

To achieve this object, the present invention provides a compound shown by the formula (1),

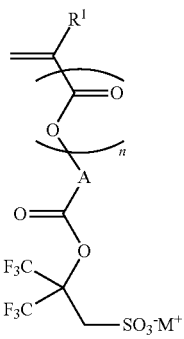

(1)

wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; "n" represents 0 or 1, provided that "n" is 0 when A is a single bond; and $M^+$ represents a cation.

Such a compound is suitable as a raw material of polymer compound usable as a base resin of a resist composition that has high resolution and high sensitivity and is excellent in balance of lithography properties such as LWR and CDU.

Furthermore, the present invention provides a polymer compound that changes by a high energy beam or heat into a polymer compound having a sulfonic acid structure shown by the formula (1a),

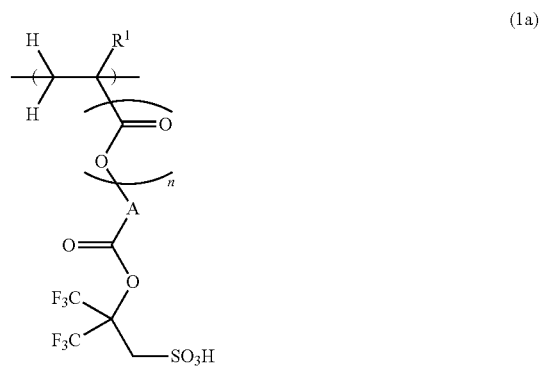

(1a)

wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; and "n" represents 0 or 1, provided that "n" is 0 when A is a single bond.

Such a polymer compound can provide a resist composition that has high resolution and high sensitivity and is excellent in balance of lithography properties such as LWR and CDU when used as a base resin of the resist composition.

Furthermore, the present invention provides a polymer compound comprising a repeating unit shown by the formula (1b),

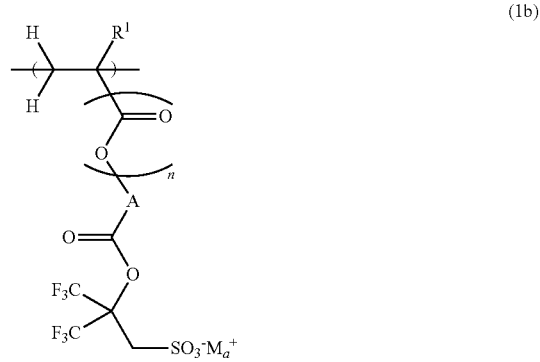

(1b)

wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; "n" represents 0 or 1, provided that "n" is 0 when A is a single bond; and $M_a^+$ represents an alkali metal cation or an ammonium cation.

Such a polymer compound can easily produce, by ion-exchange, a polymer compound that is usable as a base resin of a resist composition that has high resolution and high sensitivity and is excellent in balance of lithography properties such as LWR and CDU.

Furthermore, the present invention provides a polymer compound comprising a repeating unit shown by the formula (1c),

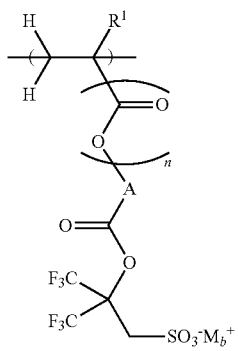

(1c)

wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; "n" represents 0 or 1, provided that "n" is 0 when A is a single bond; and $M_b^+$ represents a sulfonium cation shown by the formula (a) or an iodonium cation shown by the formula (b),

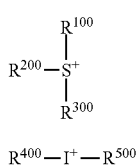

(a)

(b)

wherein $R^{100}$, $R^{200}$, $R^{300}$, $R^{400}$ and $R^{500}$ independently represent a heteroatom or a linear monovalent hydrocarbon group having 1 to 20 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom; and two or more of $R^{100}$, $R^{200}$, and $R^{300}$ may be bonded to each other to form a ring together with the sulfur atom in the formula.

Such a polymer compound can provide a resist composition that has high resolution and high sensitivity and is excellent in balance of lithography properties such as LWR and CDU when used as a base resin of the resist composition.

Each polymer compound preferably further comprises a repeating unit shown by the formula (2) and/or a repeating unit shown by the formula (3),

(2)

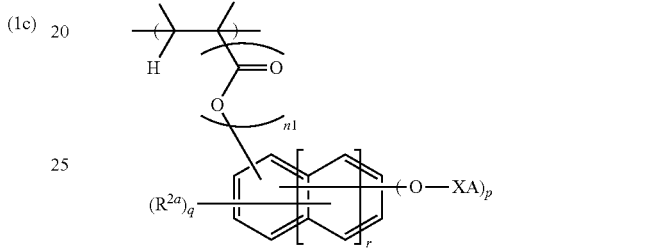

(3)

wherein $R^{1a}$ represents a hydrogen atom, a fluorine atom, a methyl group, or a trifluoromethyl group; $Z^a$ represents a single bond or (a main chain) —C(=O)—O—Z'—, where Z' represents a phenylene group, a naphthylene group, or a linear alkylene group having 1 to 10 carbon atoms or a branched or cyclic alkylene group having 3 to 10 carbon atoms, in which the alkylene group may contain a hydroxyl group, an ether bond, an ester bond, or a lactone ring; XA represents an acid-labile group; $R^{2a}$ represents a linear monovalent hydrocarbon group having 1 to 10 carbon atoms or a branched or cyclic monovalent hydrocarbon group having 3 to 10 carbon atoms, in which the hydrocarbon group may contain a heteroatom, and a part or all of hydrogen atoms in the hydrocarbon group may be substituted with a group containing a heteroatom; "p" represents an integer of 1 to 3; "q" represents a number satisfying 0≤q≤5+2r−p; "r" represents 0 or 1; and n1 represents 0 or 1.

Furthermore, the present invention provides a resist composition comprising (A) the above polymer compound and (B) an organic solvent.

Such a resist composition can form a resist film that has high resolution and high sensitivity and is excellent in balance of lithography properties such as LWR and CDU.

The resist composition preferably further comprises (C) a photo acid generator shown by the formula (4),

R—SO$_3^-$M$_b^+$ (4)

wherein $M_b^+$ represents a sulfonium cation shown by the formula (a) or an iodonium cation shown by the formula (b); R represents a hydrogen atom or a linear monovalent hydrocarbon group having 1 to 27 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom,

wherein $R^{100}$, $R^{200}$, $R^{300}$, $R^{400}$ and $R^{500}$ independently represent a heteroatom or a linear monovalent hydrocarbon group having 1 to 20 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom; and two or more of $R^{100}$, $R^{200}$, and $R^{300}$ may be bonded to each other to form a ring together with the sulfur atom in the formula.

The addition of a photo acid generator allows fine adjustment of resist properties of the resist film formed from the resist composition.

The resist composition preferably further comprises (D) a nitrogen-containing compound.

The addition of a nitrogen-containing compound allows easy adjustment of resist sensitivity of the resist film formed from the resist composition and improves various properties such as substrate adhesion, resolution, exposure margin, and pattern profile.

The resist composition preferably further comprises (E) a surfactant that is insoluble or difficulty soluble in water and soluble in an alkaline developer.

Such a resist composition can form a resist film with reduced penetration and leaching of water.

Furthermore, the present invention provides a patterning process comprising the steps of: applying the above resist composition on a substrate and baking the resist composition to form a resist film; exposing the formed resist film to a KrF excimer laser beam, an ArF excimer laser beam, an electron beam, or an EUV via a photomask; baking the exposed resist film; and then developing the resist film with a developer.

The patterning process using the inventive resist composition, which has high resolution and high sensitivity and is excellent in balance of lithography properties such as LWR and CDU, enables a fine pattern rule in photolithography.

The exposing preferably includes placing a liquid having a refractive index of 1.0 or more between the resist film and a projection lens to perform immersion exposure.

Thus the inventive patterning process can employ immersion exposure.

The immersion exposure is preferably performed by applying a top coat on the resist film and then placing the liquid having a refractive index of 1.0 or more between the top coat and the projection lens.

When a top coat film is formed on the resist film before the immersion exposure, elution from the resist film is prevented, and water-sliding property of the film surface increases.

As mentioned above, the inventive compound is suitable as a raw material of a polymer compound usable for a resist composition that has high resolution and high sensitivity and is excellent in balance of lithography properties such as LWR and CDU. Moreover, the resist composition using the inventive polymer compound as the base resin can form a resist film that has high resolution and high sensitivity, is excellent in balance of lithography properties such as LWR and CDU, has few defects, and is extremely useful for precise and fine patterning. Moreover, the inventive patterning process using such a resist composition enables a fine pattern rule in photolithography and is very effective in precise and fine patterning.

DETAILED DESCRIPTION OF THE PREFERRED EMBODIMENTS

Figure 1:
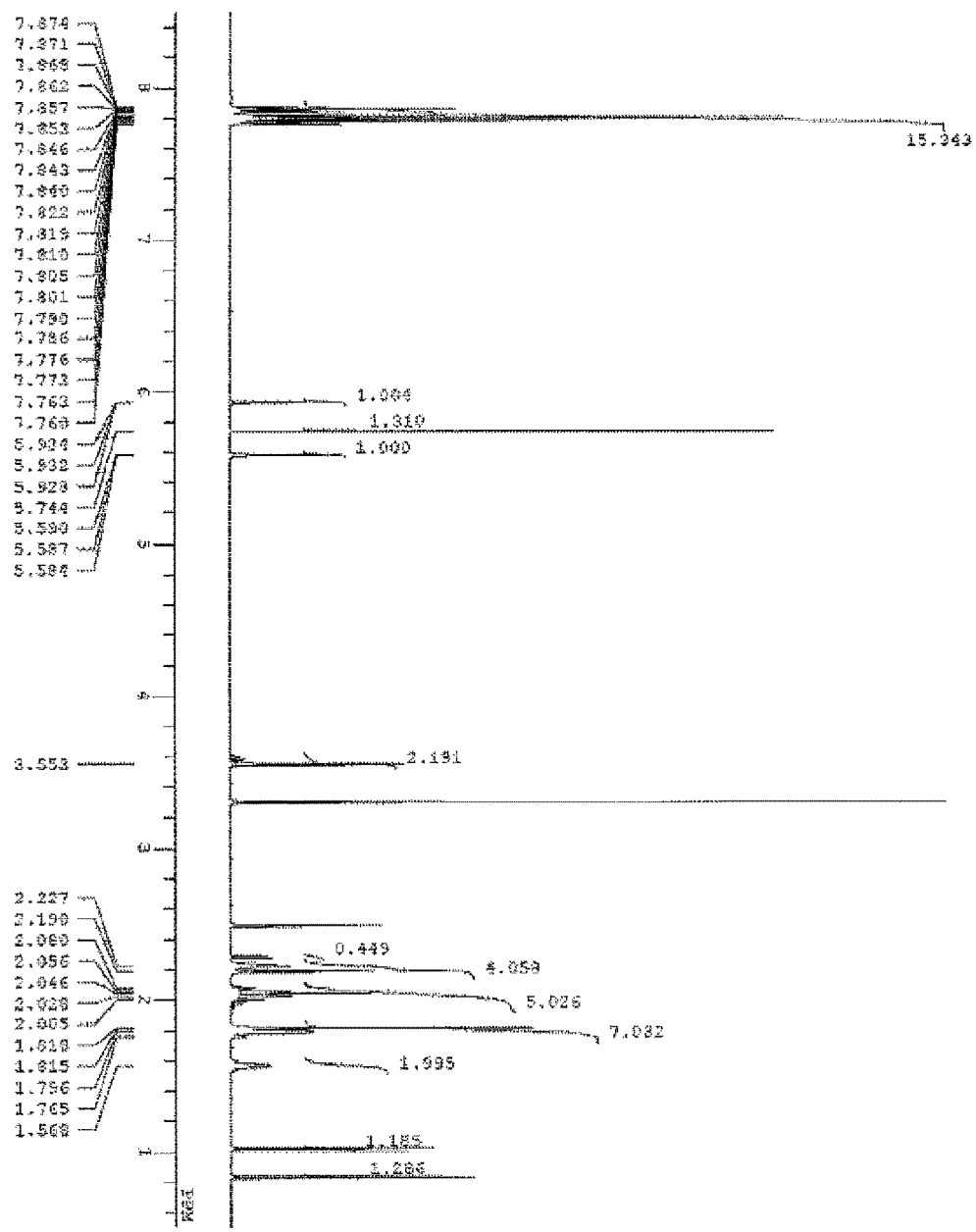
FIG. 1 is a diagram showing $^1$H-NMR/DMSO-$d_6$ of PAG Monomer 1 synthesized in Example 1-3.

As mentioned above, it has been desired to develop a resist composition that has high resolution and high sensitivity and is excellent in balance of lithography properties such as LWR and CDU. The resist composition has been required controlling diffusion of acid generated from a photo acid generator because the diffusion of generated acid causes a reduction in resolution and lithography properties. The present inventors have earnestly studied to devise a photo-decomposable repeating unit that can control the diffusion of generated acid and found that the structure containing two trifluoromethyl groups, which are electron-withdrawing groups, at the β-position of a sulfo group contributes to improvement in lithography properties of the resist composition.

The inventors have earnestly studied to accomplish the above object, and consequently found that the resist composition using, as the base resin, the polymer compound obtained by polymerizing the compound shown by the formula (1) can form a resist film that has high resolution and high sensitivity, is excellent in balance of lithography properties such as LWR and CDU, and is very effective in precise and fine patterning, thereby bringing the present invention to completion.

That is, the present invention is a compound shown by the formula (1),

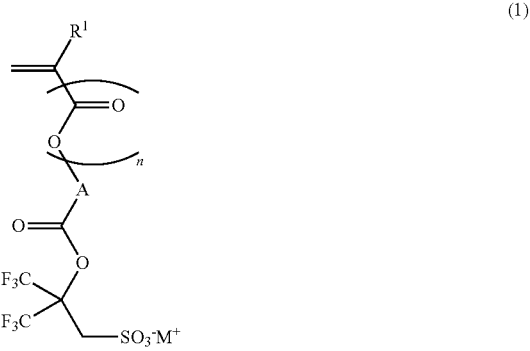

wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; "n" represents 0 or 1, provided that "n" is 0 when A is a single bond; and M+ represents a cation.

Hereinafter, the present invention will be described in detail, but the present invention is not limited thereto.

<Compound Shown by Formula (1)>

The present invention provides the compound shown by the formula (1).

In the formula (1), A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom. Illustrative examples thereof include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, and a heptadecane-1,17-diyl group; saturated cyclic hydrocarbon groups such as a cyclopentanediyl group, a cyclohexanediyl group, a norbornanediyl group, and an adamantanediyl group; and unsaturated cyclic hydrocarbon groups such as a phenylene group and a naphthylene group. In addition, a part of hydrogen atoms in these groups may be substituted with an alkyl group such as a methyl group, an ethyl group, a propyl group, a n-butyl group, and a tert-butyl group. Also, these group may contain a heteroatom such as an oxygen atom, a sulfur atom, a nitrogen atom, and a halogen atom, and a part or all of hydrogen atoms in the groups may be substituted with a group containing a heteroatom such as an oxygen atom, a sulfur atom, a nitrogen atom, and a halogen atom so as to form a hydroxyl group, a cyano group, a carbonyl group, an ether bond, an ester bond, a sulfonate ester bond, a carbonate bond, a lactone ring, a sultone ring, a carboxylic anhydride, a haloalkyl group or the like. In view of availability of raw materials, unsubstituted alkylene groups, a phenylene group, and a naphthylene group are preferable.

Illustrative examples of the anion structure of the compound shown by the formula (1) are shown below.

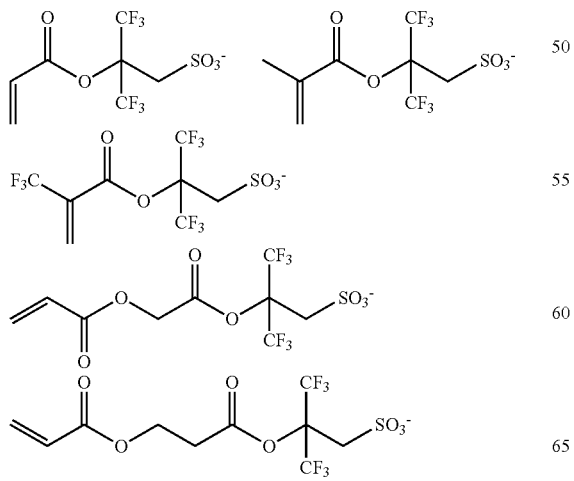

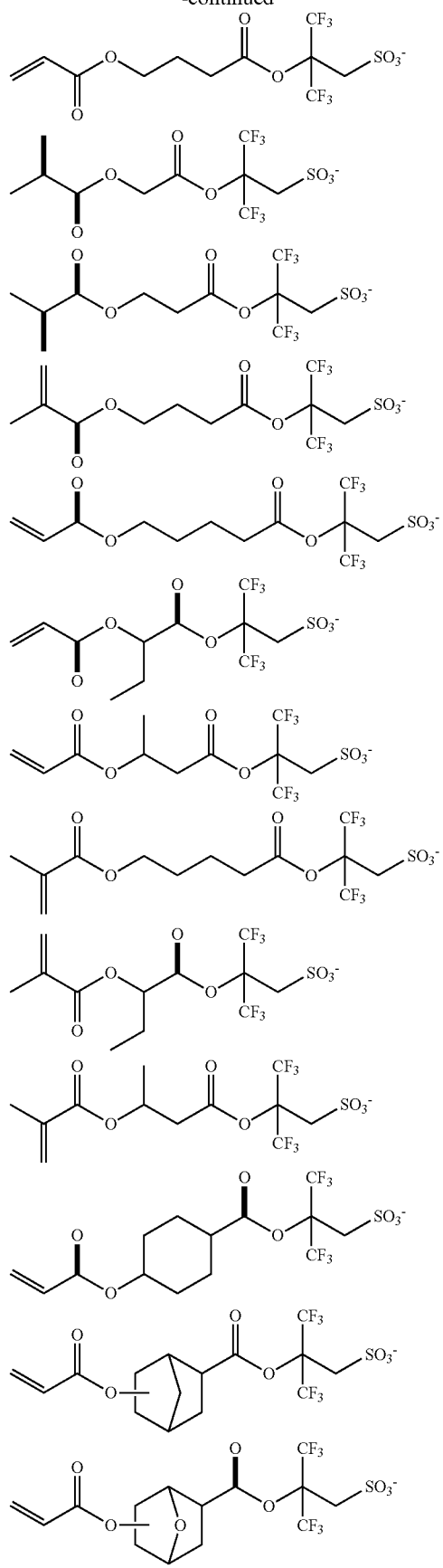

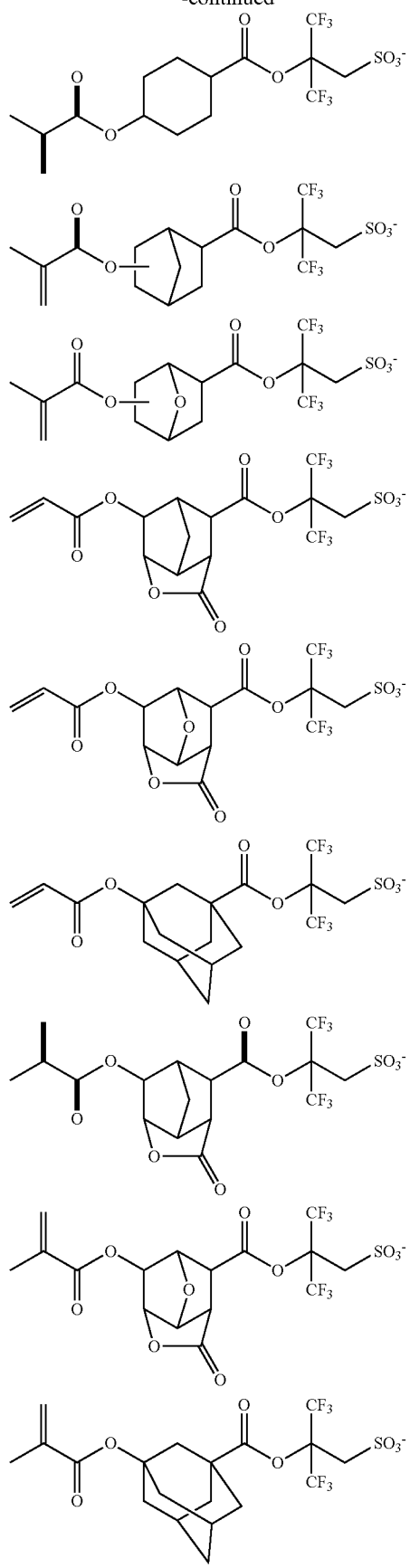
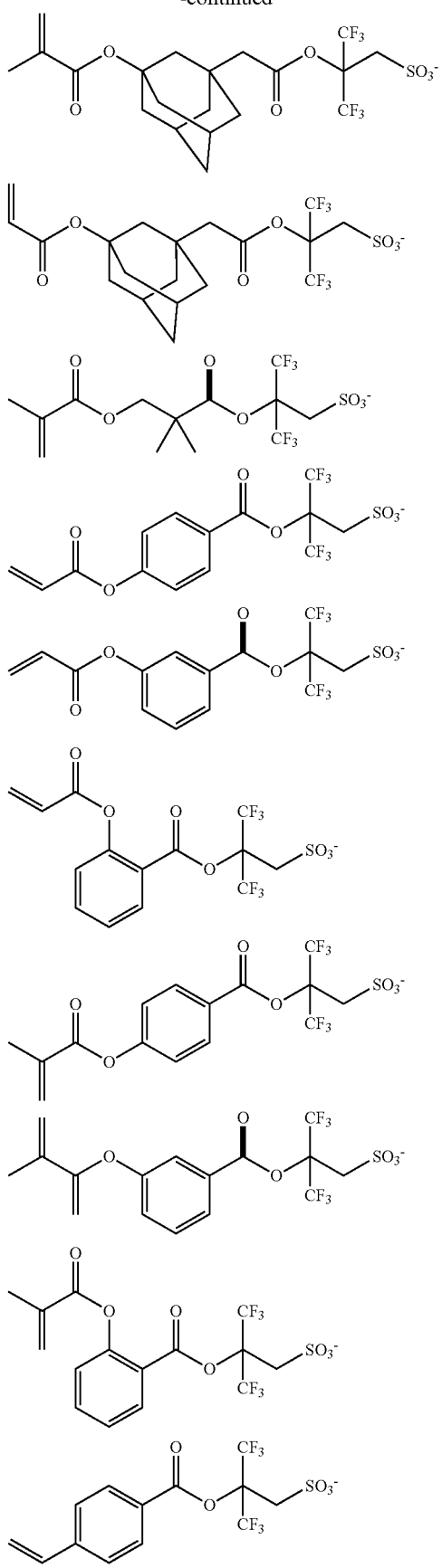

-continued

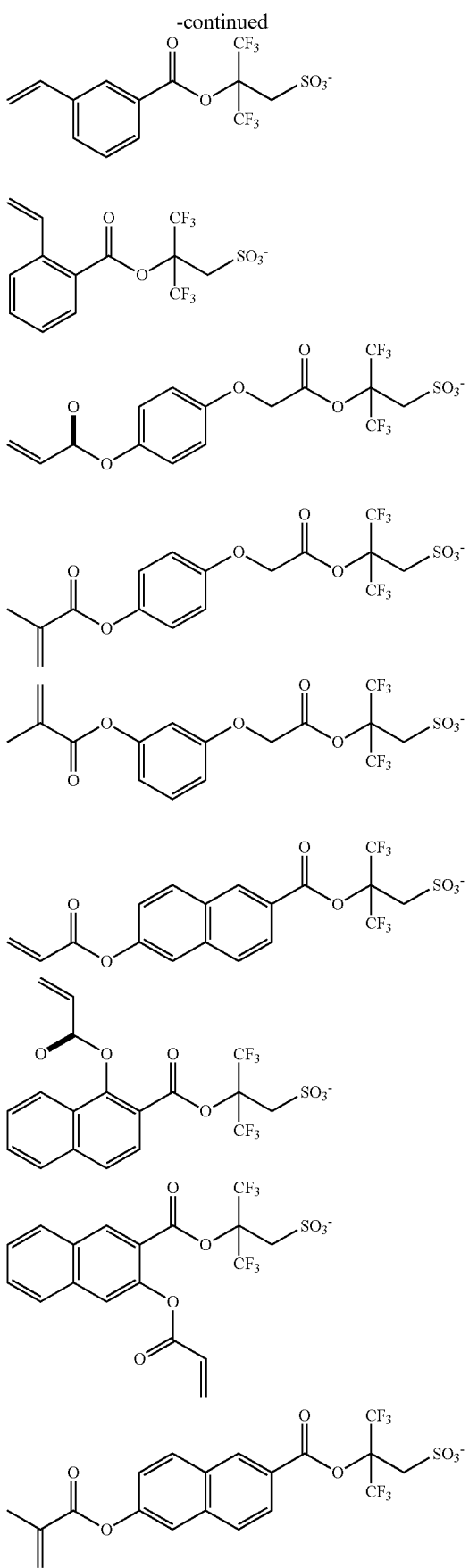

-continued

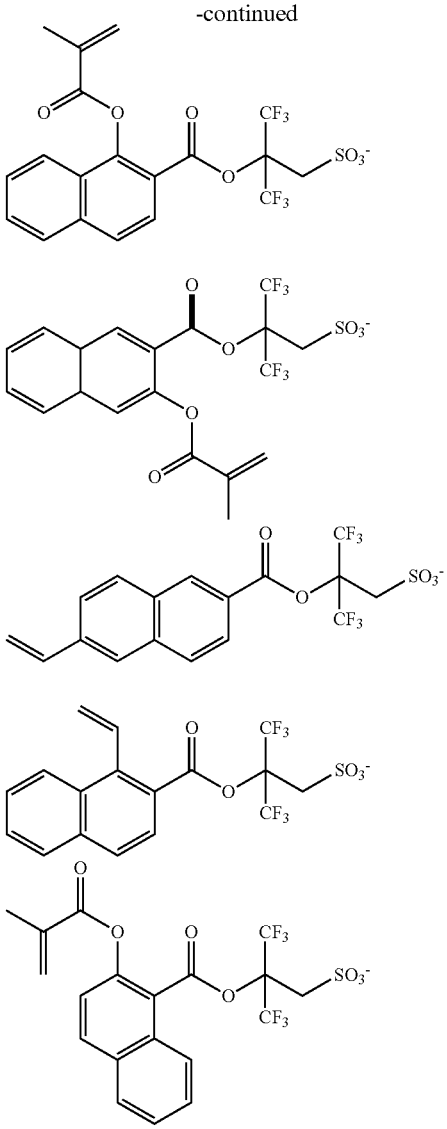

Examples of M+ include alkali metal cations such as lithium cation, sodium cation, and potassium cation, ammonium cations, sulfonium cations, and iodonium cations. As the ammonium cation, tetramethylammonium cation, tetraethylammonium cation, benzyltrimethylammonium cation, and triethylammonium cation are particularly preferable.

In addition, the compound shown by the formula (1) allows various structural design by variously combining A in the anion structure and the cation M+. Thus, this compound allows an appropriate structural design according to use and change of the wavelength of exposure light, other copolymerization units in the base resin, and a casting solvent in the resist composition.

The compound shown by the formula (1) may have an appropriate structure combining the aforementioned anion and cation structures, although the inventive compound shown by the formula (I) is not limited to the above structure.

A method for synthesizing the compound shown by the formula (1) will be now described. The following scheme shows a procedure of an exemplary synthesis method.

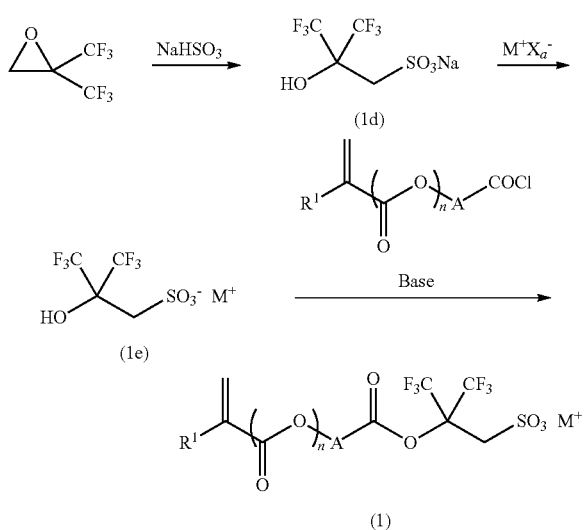

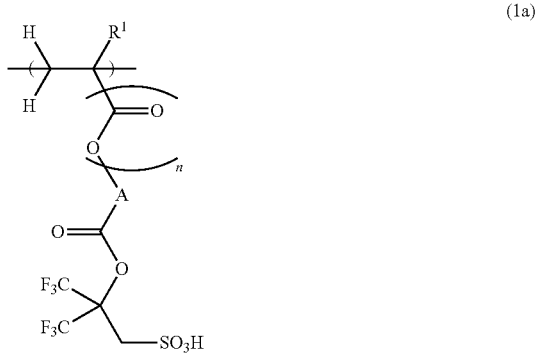

(1)

wherein $M^+$, $R^1$, and A are as defined above; $X_a^-$ represents an anion such as $I^-$, $Br^-$, $Cl^-$, $CH_3SO_4^-$, and $CH_3SO_3^-$.

In the above method, 2,2-bistrifluoromethyloxirane first reacts with a sulfur compound such as sulfite and hydrogen sulfite to synthesize an onium salt shown by the formula (1d) as an intermediate. The sulfur compound used as the reaction agent is preferably sodium hydrogen sulfite because of inexpensiveness and handleability.

Then, the resulting intermediate shown by the formula (1d) is subjected to ion-exchange with a sulfonium salt such as sulfonium halide to synthesize an onium salt compound shown by the formula (1e). Meanwhile, the ion-exchange reaction is elaborated in Japanese Patent Laid-Open Publication No. 2007-145797, for example.

Then, the resulting onium salt compound shown by the formula (1e) is acylated to obtain the compound shown by the formula (1). The acylation may be done in a usual organic chemical manner. For example, as shown in the above scheme, the onium salt compound shown by the formula (1e) may react with oxychloride under a basic condition.

The inventive compound, as described above, is suitable as a raw material of a polymer compound usable as a base resin of a resist composition that has high resolution and high sensitivity and is excellent in balance of lithography properties such as LWR and CDU.

<Polymer Compound that Changes into Polymer Compound Having Sulfonic Acid Structure Shown by Formula (1a)>

Furthermore, the present invention provides a polymer compound that changes by a high energy beam or heat into a polymer compound having a sulfonic acid structure shown by the formula (1a), wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; and "n" represents 0 or 1, provided that "n" is 0 when A is a single bond.

Illustrative examples of A in the formula (1a) include the same examples as A in the formula (1).

The inventive polymer compound that changes into the polymer compound having the sulfonic acid structure shown by the formula (1a) may be, for example, a polymer compound having a repeating unit shown by the formula (1c), which decomposes by photo exposure and thereby changes into the polymer compound having the sulfonic acid structure shown by the formula (1a), as shown below.

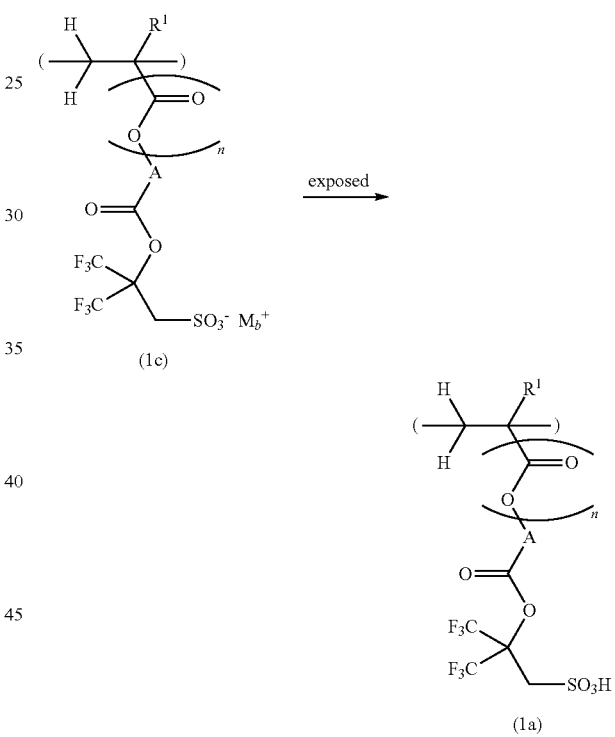

wherein $R^1$, A, and "n" are as defined above; and $M_b^+$ represents a sulfonium cation or an iodonium cation.

The inventive polymer compound that changes into the polymer compound having the sulfonic acid structure shown by the formula (1a) contains an anion part of a photo acid generator as a repeating unit. This structure can significantly reduce the diffusion of generated acid. Such idea has been reported several times in the past. For example, Japanese Patent Laid-Open Publication No. 2008-133448 and No. 2010-077404 disclose resist compositions using a polymer compound incorporated with a repeating unit of photo acid generator having a specific anion structure. However, these resist compositions have worse lithography properties, such as LWR and CDU, than the resist composition using the inventive polymer compound as a base polymer. The reason is supposed as follows.

The photo-decomposable repeating units disclosed in the publications are α-fluorosulfonic acid containing an electron-withdrawing fluorine atom at the α-position of the sulfo group. Thus, these repeating units generate too strong acid to sufficiently reduce the diffusion of generated acid. Although the acid generator unit is incorporated in the base resin, the photo-decomposable repeating units disclosed in these publications are still insufficient to reduce the acid diffusion in the application of the ArF immersion lithography, electron beam lithography, and EUV lithography for forming a fine pattern of 32-nm or finer node.

On the other hand, the sulfonic acid-generating repeating unit contained in the inventive polymer compound has two trifluoromethyl groups, which are electron-withdrawing groups, at the β-position of the sulfo group. This repeating unit generates weaker acid than α-fluorosulfonic acid. Thus, this acid causes less acid-labile groups to be cleaved from the sulfonic acid-generating repeating unit contained in the inventive polymer compound than α-fluorosulfonic acid, causing an apparently low acid diffusion length. This is supposed to be the reason of improving LWR and CDU, which are especially affected by the acid diffusion.

In the case of incorporating a photo-decomposable repeating unit having a structure that generates a sulfonic acid having an electron-withdrawing group at neither the α-position nor the β-position of the sulfo group or a sulfonic acid having only one electron-withdrawing group at the β-position, the acidity is too weak to cleave an acid-labile group, resulting in low sensitivity and low resolution. In other words, the inventive polymer compound containing the photo-decomposable repeating unit contributes to improvement in lithography properties of the resist composition by virtue of the optimum structural design of the repeating unit.

The inventive polymer compound that changes into the polymer compound having the sulfonic acid structure shown by the formula (1a) preferably further contains a repeating unit shown by the formula (2) and/or a repeating unit shown by the formula (3),

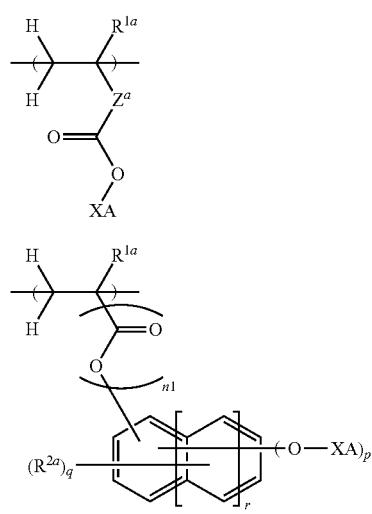

wherein $R^{1a}$ represents a hydrogen atom, a fluorine atom, a methyl group, or a trifluoromethyl group; $Z^a$ represents a single bond or (a main chain) —C(=O)—O—Z'—, where Z' represents a phenylene group, a naphthylene group, or a linear alkylene group having 1 to 10 carbon atoms or a branched or cyclic alkylene group having 3 to 10 carbon atoms, in which the alkylene group may contain a hydroxyl group, an ether bond, an ester bond, or a lactone ring; XA represents an acid-labile group; $R^{2a}$ represents a linear monovalent hydrocarbon group having 1 to 10 carbon atoms or a branched or cyclic monovalent hydrocarbon group having 3 to 10 carbon atoms, in which the hydrocarbon group may contain a heteroatom, and a part or all of hydrogen atoms in the hydrocarbon group may be substituted with a group containing a heteroatom; "p" represents an integer of 1 to 3; "q" represents a number satisfying 0≤q≤5+2r−p; "r" represents 0 or 1; and n1 represents 0 or 1.

Illustrative examples of the repeating unit shown by the formula (2) are described in paragraphs (0014) to (0054) of Japanese Patent Laid-Open Publication No. 2014-225005. In the repeating unit shown by the formula (2), the most preferable structure of the acid-labile group is, for example, a tertiary ester structure containing an alicyclic group.

Illustrative examples of the repeating unit shown by the formula (3) include the following repeating units. In particular, repeating units containing a phenylene group are preferable.

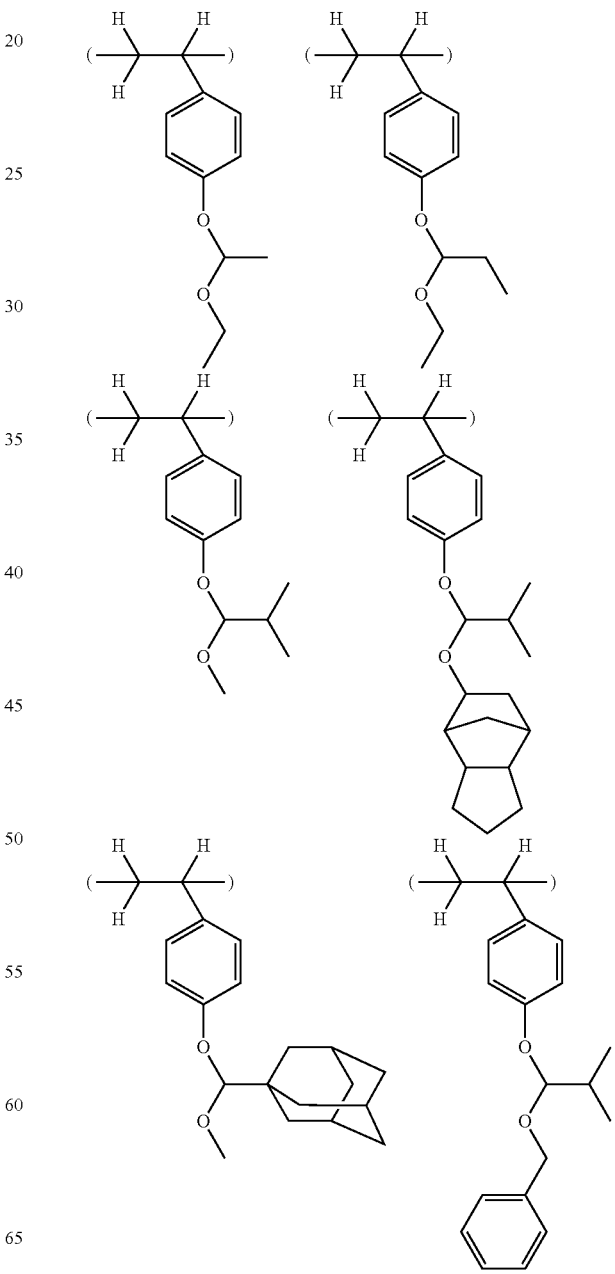

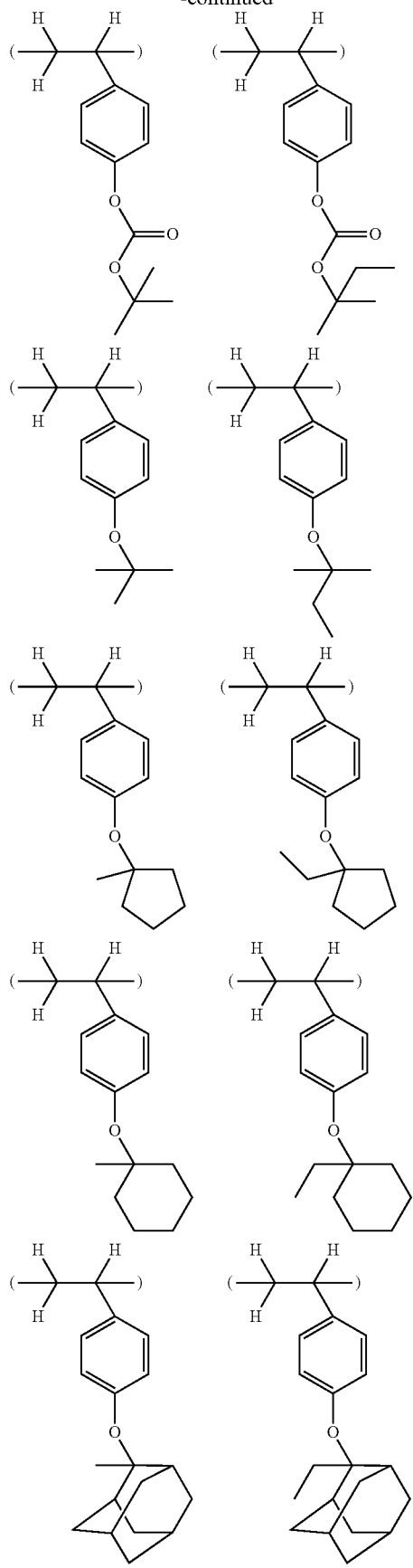
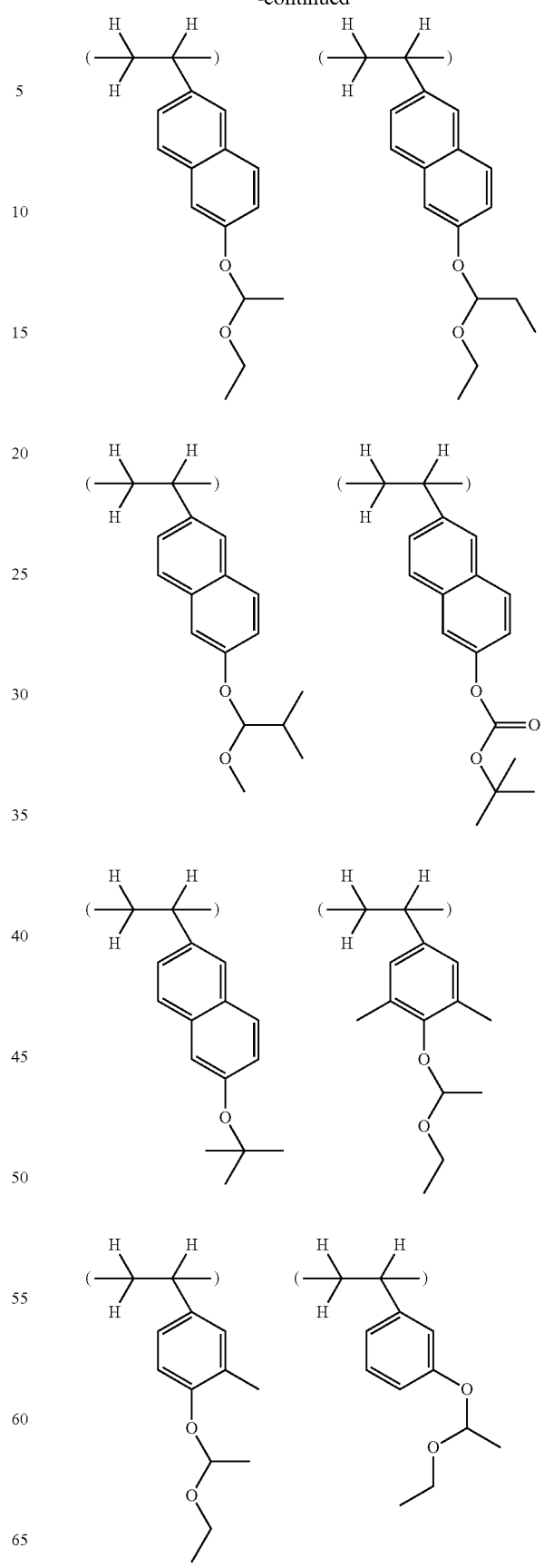

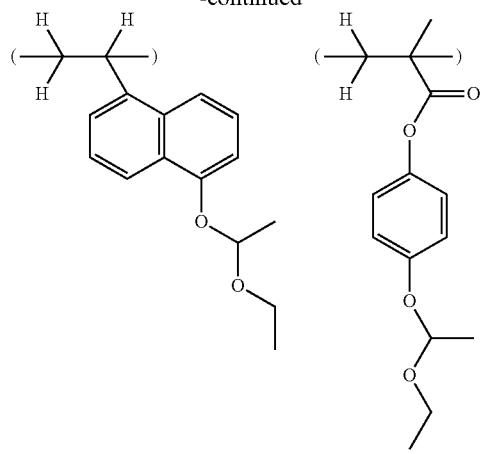
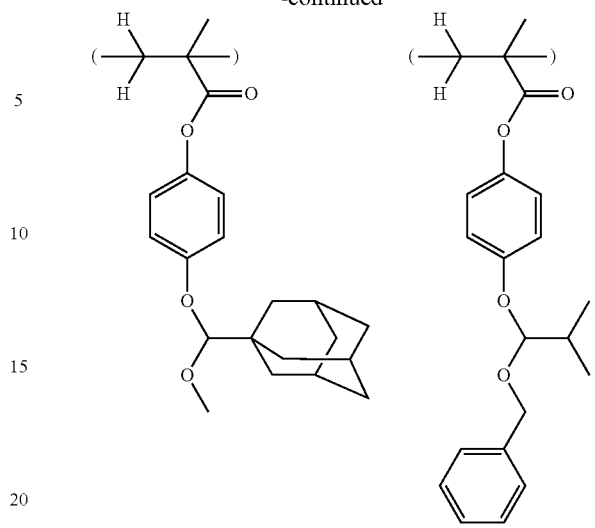
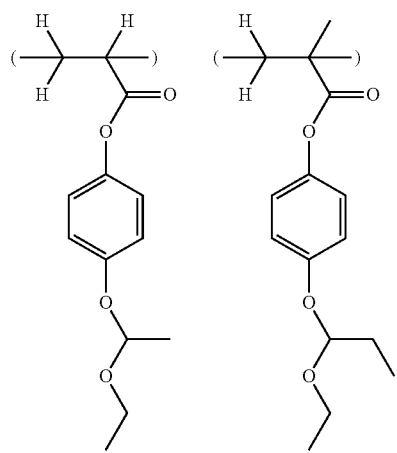
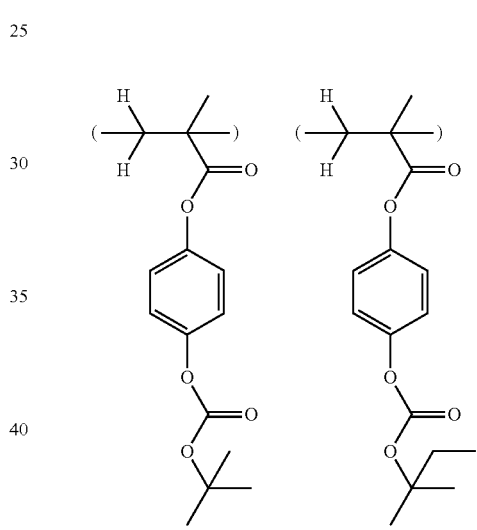
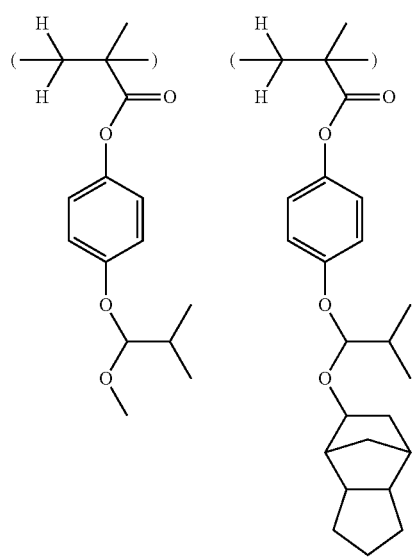
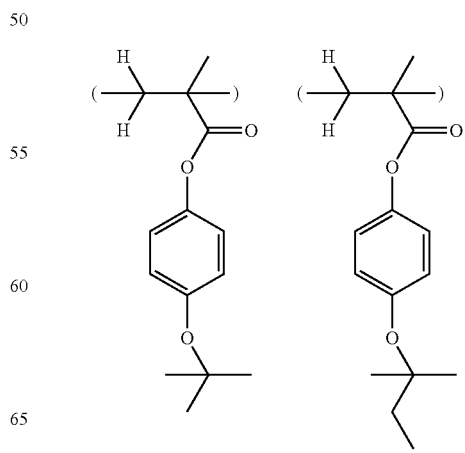

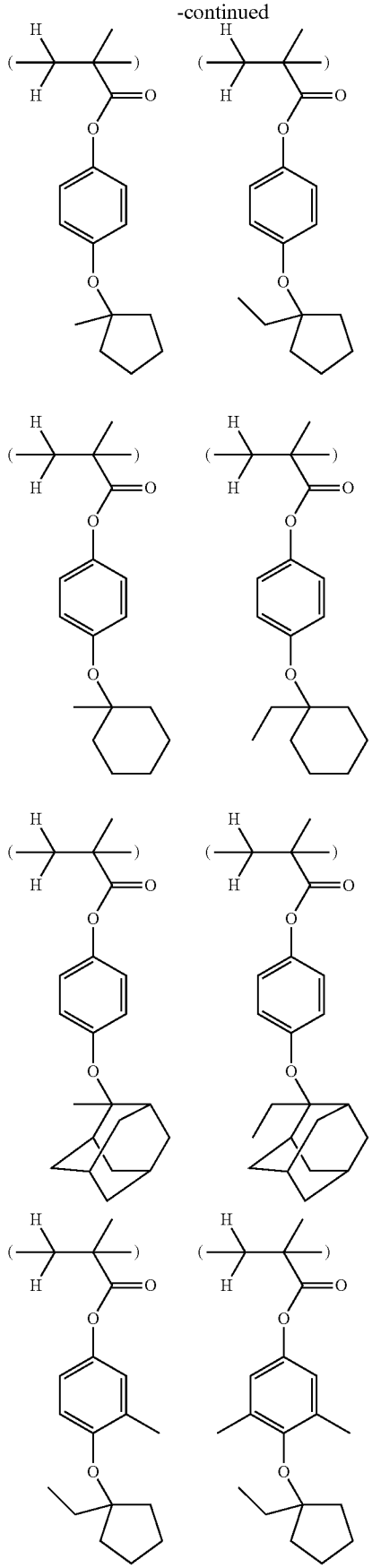

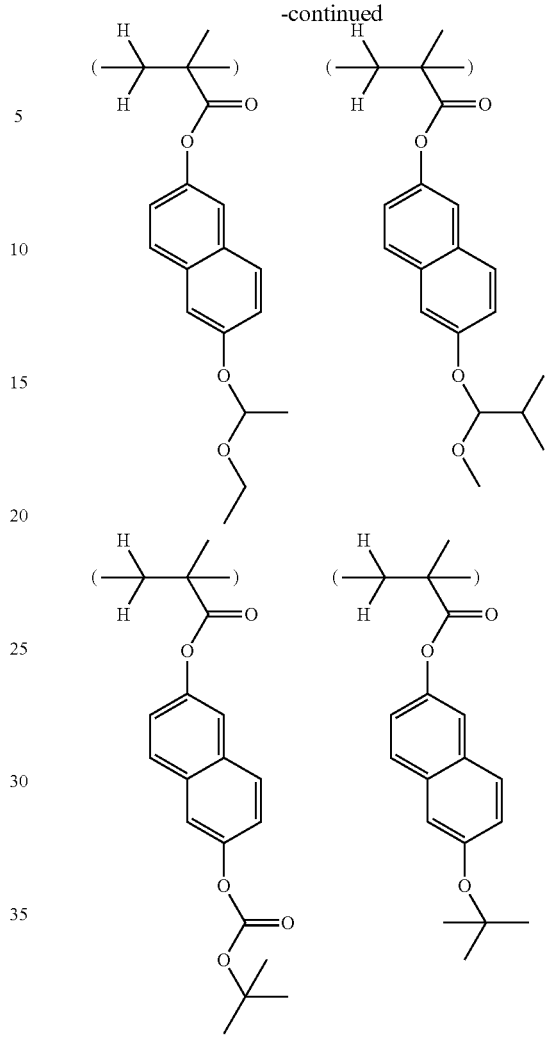

The inventive polymer compound that changes into the polymer compound having the sulfonic acid structure shown by the formula (1a) preferably further contains a repeating unit shown by the formula (p1) or a repeating unit shown by the formula (p2),

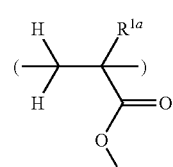

(p1)

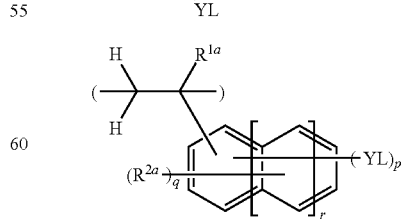

(p2)

wherein $R^{1a}$, $R^{2a}$, "p", "q", and "r" are as defined above; YL represents a hydrogen atom or a polar group having one or more structures selected from a hydroxyl group, a cyano group, a carbonyl group, a carboxyl group, an ether bond, an ester bond, a sulfonate ester bond, a carbonate bond, a lactone ring, a sultone ring, and a carboxylic anhydride.
Illustrative examples of the repeating unit shown by the formula (p1) include the following repeating units although the present invention is not limited thereto.
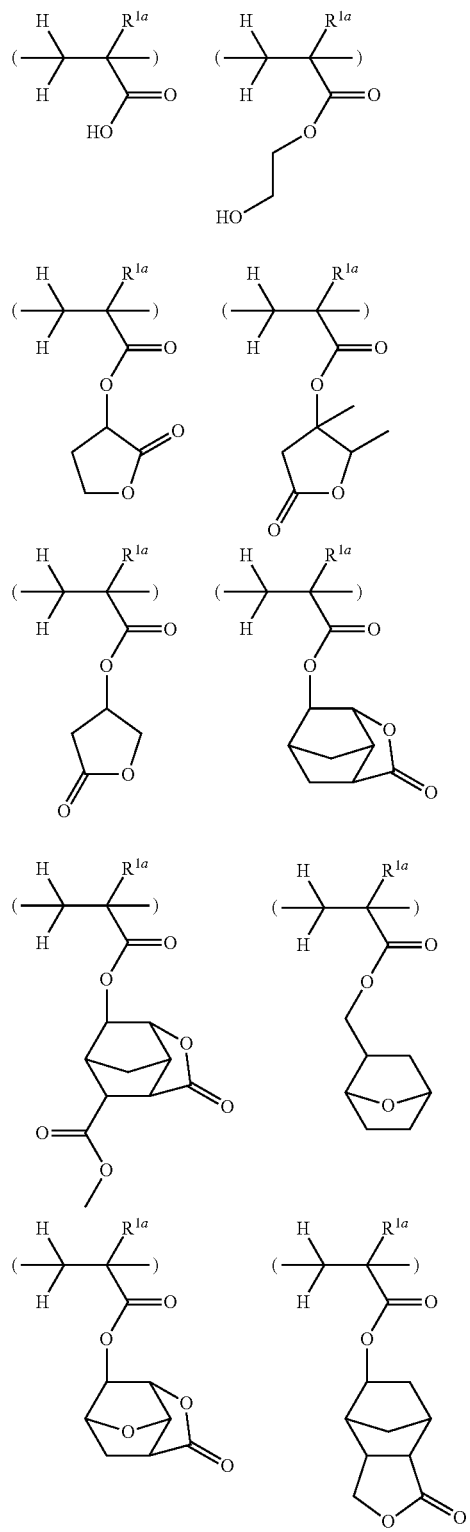
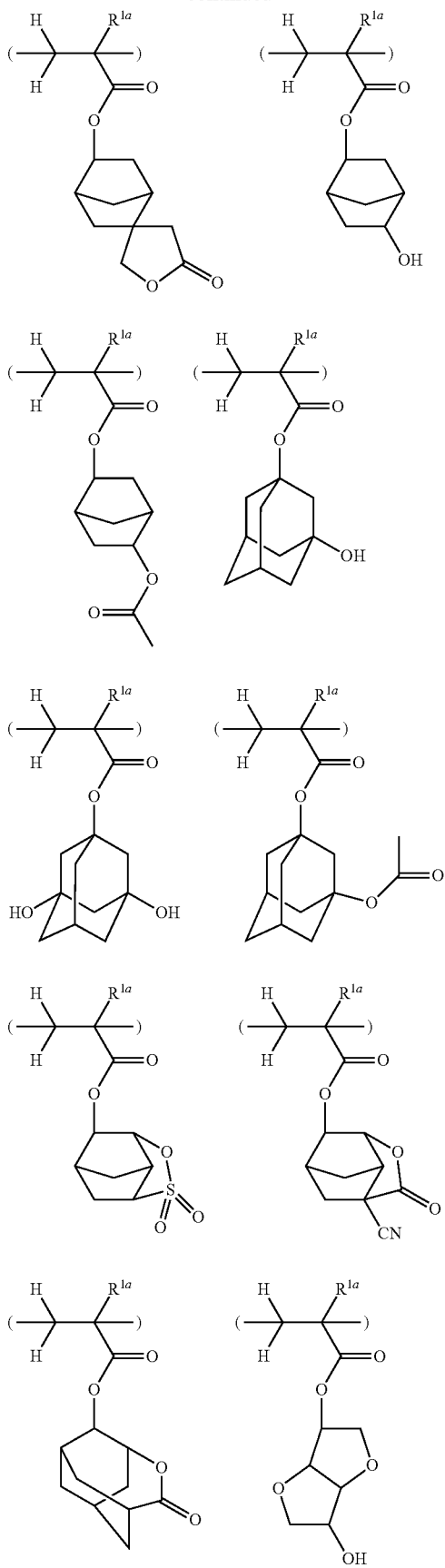

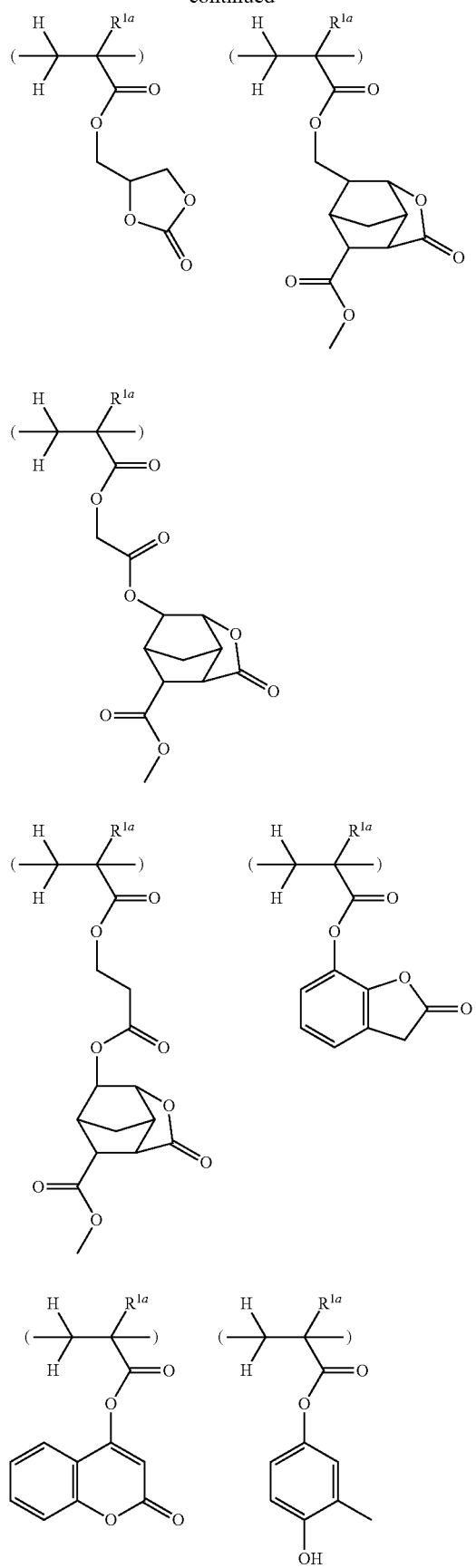
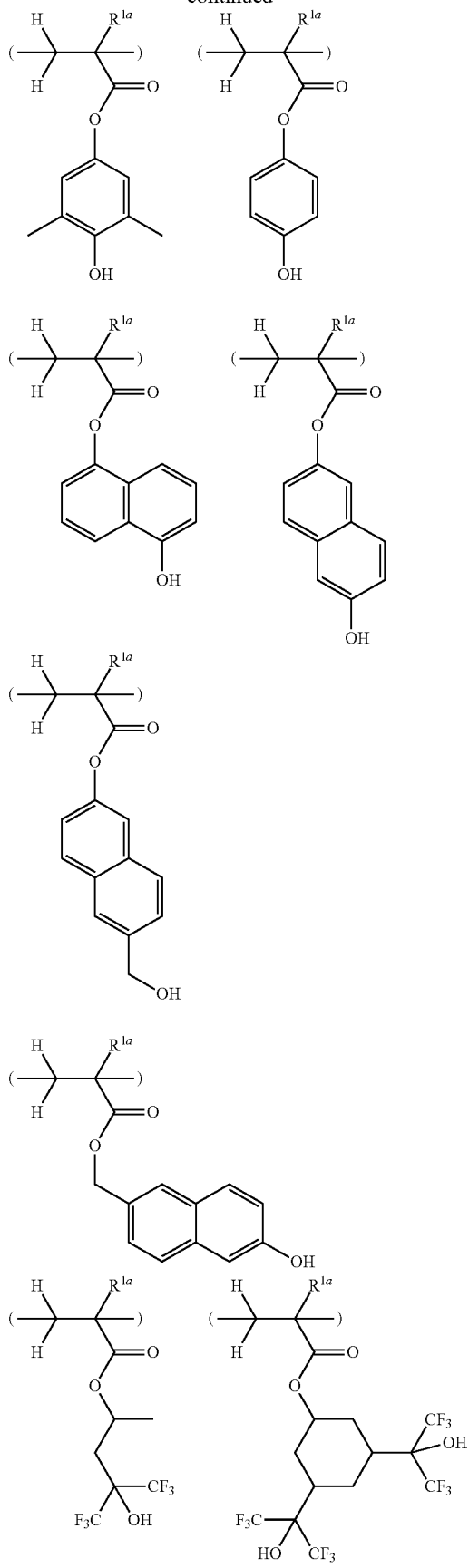

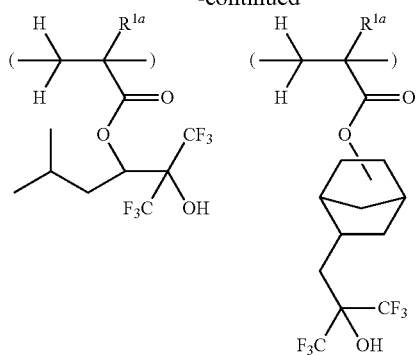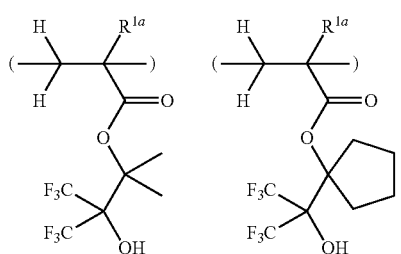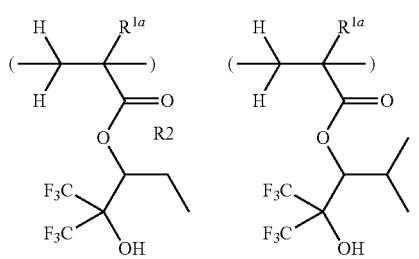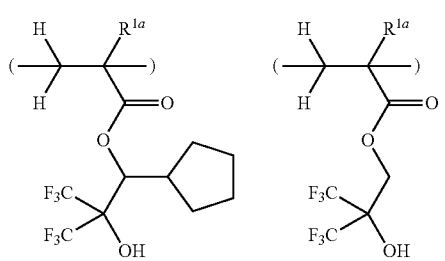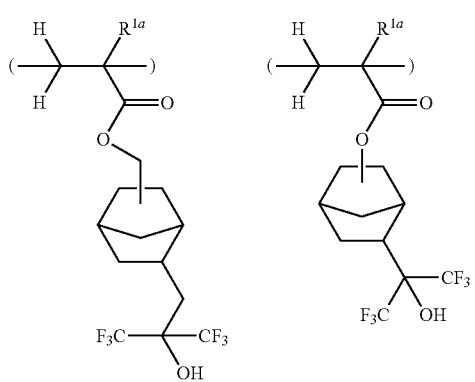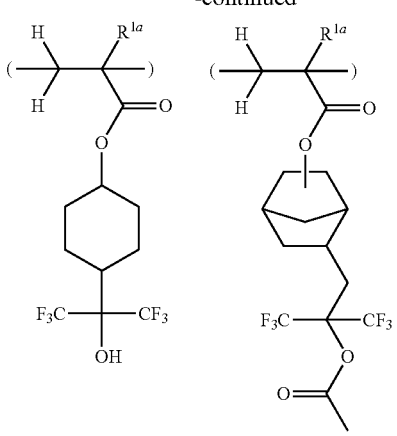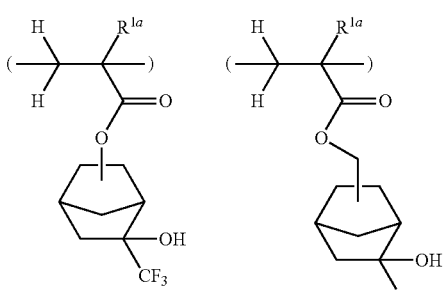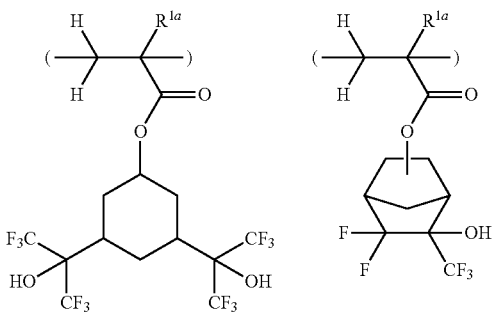
Illustrative examples of the repeating unit shown by the formula (p2) include the following repeating units although the present invention is not limited thereto.
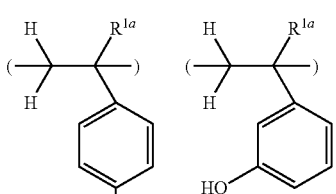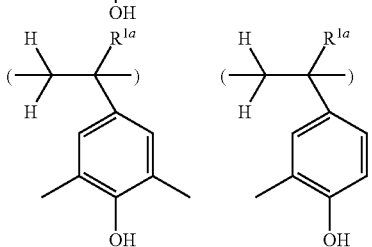

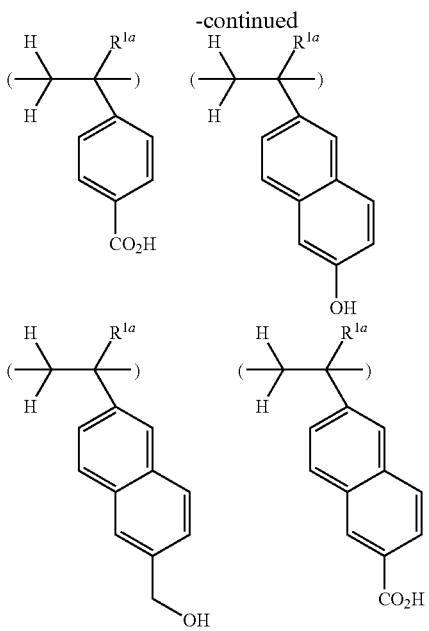

When the polymer compound containing the repeating unit shown by the formula (p1) or (p2) is used as the base resin of the resist composition, substrate adhesion of the resist composition can be improved, and dissolution rate with respect to a developer can be adjusted.

The inventive polymer compound that changes into the polymer compound having the sulfonic acid structure shown by the formula (1a) may further contain a repeating unit shown by the formula (d1) or a repeating unit shown by the formula (d2),

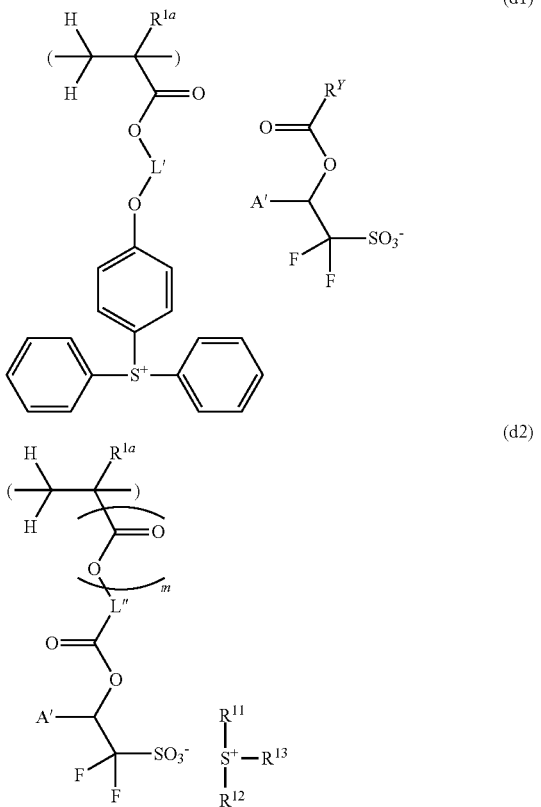

wherein $R^{1a}$ is as defined above; L' represents a single bond or an alkylene group having 2 to 5 carbon atoms; $R^Y$ represents a linear monovalent hydrocarbon group having 1 to 20 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom; A' represents a hydrogen atom or a trifluoromethyl group; $R^{11}$, $R^{12}$, and $R^{13}$ each represent a linear, branched, or cyclic alkyl or alkenyl group having 1 to 10 carbon atoms or an aryl group having 6 to 18 carbon atoms, in which these groups may contain a heteroatom, and a part or all of hydrogen atoms in these groups may be substituted with a group containing a heteroatom; two of $R^{11}$, $R^{12}$, and $R^{13}$ may be bonded to each other to form a ring together with the sulfur atom in the formula; L" represents a single bond or a linear divalent hydrocarbon group having 1 to 20 carbon atoms or a branched or cyclic divalent hydrocarbon group having 3 to 20 carbon atoms, in which the hydrocarbon group may contain a heteroatom, and a part or all of hydrogen atoms in the hydrocarbon group may be substituted with a group containing a heteroatom; "m" represents 0 or 1, provided that "m" is 0 when L" is a single bond.

Illustrative examples of L" in the formula (d1) include a single bond, an ethylene group, a propylene group, and a butylene group.

Illustrative examples of the anion structure in the formula (d1) include anion structures described in paragraphs (0100) and (0101) of Japanese Patent Laid-Open Publication No. 2014-177407.

Illustrative examples of the structure of the formula (d2) include those described in paragraphs (0021) to (0027) of Japanese Patent Laid-Open Publication No. 2010-77404 and paragraphs (0021) to (0028) of Japanese Patent Laid-Open Publication No. 2010-116550.

The inventive polymer compound that changes into the polymer compound having the sulfonic acid structure shown by the formula (1a) may further contain a repeating unit having a structure in which an alcoholic hydroxyl group is protected by an acid-labile group. Such a repeating unit has one or more alcoholic hydroxyl groups protected by protective groups which decompose by the action of acid to produce the alcoholic hydroxyl groups, although not limited to a particular structure. Illustrative examples thereof include those described in paragraphs (0055) to (0065) of Japanese Patent Laid-Open Publication No. 2014-225005.

Moreover, the inventive polymer compound that changes into the polymer compound having the sulfonic acid structure shown by the formula (1a) may further contain other repeating units obtained by polymerizing monomers. Examples of the monomer include substituted acrylates such as methyl methacrylate, methyl crotonate, dimethyl maleate, and dimethyl itaconate; unsaturated carboxylic acids such as maleic acid, fumaric acid, and itaconic acid; cyclic olefins such as norbornene, norbornene derivatives, and tetracyclo[$6.2.1.1^{3,6}.0^{2,7}$]dodecene derivatives; unsaturated anhydrides such as itaconic anhydride; aromatic compounds such as indene and acenaphthylene. In addition, hydrogenated ring-opening metathesis polymers described in Japanese Patent Laid-Open Publication No. 2003-66612 can also be used.

The inventive polymer compound that changes into the polymer compound having the sulfonic acid structure shown by the formula (1a) preferably has a weight average molecular weight of 1,000 to 500,000, more preferably 3,000 to 100,000. When the weight average molecular weight of the polymer compound is in this range, it is possible to prevent an excessive reduction in etching resistance and a reduction in resolution due to lack of dissolution rate difference between before and after exposure. The molecular weight can be measured by gel permeation chromatography (GPC) in terms of polystyrene.

In the inventive polymer compound that changes into the polymer compound having the sulfonic acid structure shown by the formula (1a), preferable content ratio (mol %) of each repeating unit is, for example, as shown below, although the ratio is not limited to this range.

The inventive polymer compound that changes into the polymer compound having the sulfonic acid structure shown by the formula (1a) preferably contains:
(I) one or more repeating units that change into the repeating unit shown by the formula (1a) in an amount of 1 to 30 mol %, preferably 1 to 20 mol %, more preferably 1 to 10 mol % in total;
(II) one or more repeating units shown by the formula (2) or (3) in an amount of 1 mol % or more and 60 mol % or less, preferably 5 to 50 mol %, more preferably 10 to 50 mol % in total;
(III) one or more repeating units shown by the formula (p1) or (p2) in an amount of 0 mol % or more and 60 mol % or less, preferably 5 to 50 mol %, more preferably 10 to 50 mol % in total, as needed;
(IV) one or more repeating units shown by the formula (d1) or (d2) in an amount of 0 to 30 mol %, preferably 0 to 20 mol %, more preferably 0 to 10 mol % in total, as needed; and
(V) one or more repeating units based on other monomers in an amount of 0 to 80 mol %, preferably 0 to 70 mol %, more preferably 0 to 50 mol % in total, as needed.

The inventive polymer compound as described above can provide a resist composition that has high resolution and high sensitivity and is excellent in balance of lithography properties such as LWR and CDU when used as a base resin of the resist composition.

<Polymer Compound Containing Repeating Unit Shown by Formula (1b)>

Furthermore, the present invention provides a polymer compound containing a repeating unit shown by the formula (1b),

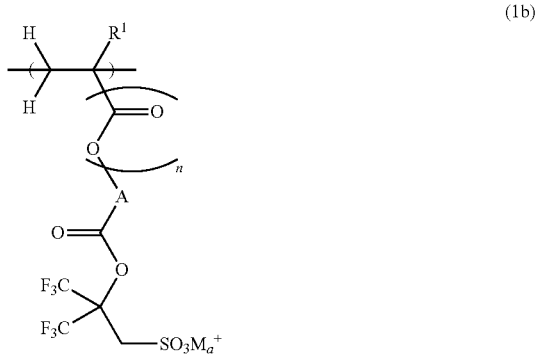

(1b)

wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; "n" represents 0 or 1, provided that "n" is 0 when A is a single bond; and $M_a^+$ represents an alkali metal cation or an ammonium cation.

Illustrative examples of A in the formula (1b) include the same examples as A in the formula (1).

In the formula (1b), $M_a^+$ represents an alkali metal cation or an ammonium cation. More specifically, $M_a^+$ is preferably lithium cation, sodium cation, potassium cation, or ammonium cation. As the ammonium cation, tetramethylammonium cation, tetraethylammonium cation, benzyltrimethylammonium cation, and triethylammonium cation are particularly preferable. When $M_a^+$ is such cation species, $M_a^+X^-$ produced after ion-exchange is hydrophilic and is easily removed. Thus, the reaction proceeds advantageously.

Moreover, the inventive polymer compound containing the repeating unit shown by the formula (1b) may contain the repeating units shown by the formulae (2), (3), (p1), (p2), (d1), and (d2) and repeating units based on other monomers, which are mentioned above as the repeating units that may be contained in the polymer compound that changes into the polymer compound having the sulfonic acid structure shown by the formula (1a).

The inventive polymer compound containing the repeating unit shown by the formula (1b) preferably has a weight average molecular weight of 1,000 to 500,000, more preferably 3,000 to 100,000. When the weight average molecular weight is in this range, it is possible to prevent an excessive reduction in etching resistance and a reduction in resolution due to lack of dissolution rate difference between before and after exposure. The molecular weight can be measured by gel permeation chromatography (GPC) in terms of polystyrene.

In the inventive polymer compound containing the repeating unit shown by the formula (1b), preferable content ratio (mol %) of each repeating unit is, for example, as shown below, although the ratio is not limited to this range.

The inventive polymer compound containing the repeating unit shown by the formula (1b) preferably contains:
(I) one or more repeating units shown by the formula (1b) in an amount of 1 to 30 mol %, preferably 1 to 20 mol %, more preferably 1 to 10 mol % in total;
(II) one or more repeating units shown by the formula (2) or (3) in an amount of 1 mol % or more and 60 mol % or less, preferably 5 to 50 mol %, more preferably 10 to 50 mol % in total;
(III) one or more repeating units shown by the formula (p1) or (p2) in an amount of 0 mol % or more and 60 mol % or less, preferably 5 to 50 mol %, more preferably 10 to 50 mol % in total, as needed;
(IV) one or more repeating units shown by the formula (d1) or (d2) in an amount of 0 to 30 mol %, preferably 0 to 20 mol %, more preferably 0 to 10 mol % in total, as needed; and
(V) one or more repeating units based on other monomers in an amount of 0 to 80 mol %, preferably 0 to 70 mol %, more preferably 0 to 50 mol % in total, as needed.

The inventive polymer compound containing the repeating unit shown by the formula (1b) can be synthesized by, for example, adding a radical polymerization initiator to a compound shown by the formula (1) in which $M^+=M_a^+$ in an organic solvent to initiate radical polymerization. If necessary, compounds for forming other repeating units may be added thereto for the radical polymerization.

Illustrative examples of the organic solvent used in the polymerization include toluene, benzene, tetrahydrofuran, diethyl ether, and dioxane. Illustrative examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. The heating temperature is preferably 50 to 80° C. The reaction time is 2 to 100 hours, preferably 5 to 20 hours.

The acid-labile group contained in the formula (2) and so on may be an acid-labile group that has been introduced into a monomer as it is, or may be protected or partially protected after polymerization.

The inventive polymer compound as described above can easily produce, by ion-exchange, a polymer compound that is usable as a base resin of a resist composition that has high resolution and high sensitivity and is excellent in balance of lithography properties such as LWR and CDU.

<Polymer Compound Containing Repeating Unit Shown by Formula (1c)>

Furthermore, the present invention provides a polymer compound containing a repeating unit shown by the formula (1c),

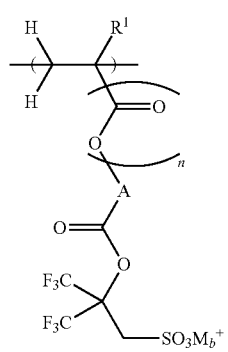

(1c)

wherein $R^1$ represents a hydrogen atom, a fluorine atom, a methyl group, or a trifluoromethyl group; A represents a single bond or a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; "n" represents 0 or 1, provided that "n" is 0 when A is a single bond; and $M_b^+$ represents a sulfonium cation shown by the formula (a) or an iodonium cation shown by the formula (b),

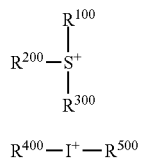

(a)

(b)

wherein $R^{100}$, $R^{203}$, $R^{300}$, $R^{400}$ and $R^{500}$ independently represent a heteroatom or a linear monovalent hydrocarbon group having 1 to 20 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom; and two or more of $R^{100}$, $R^{200}$, and $R^{300}$ may be bonded to each other to form a ring together with the sulfur atom in the formula.

Illustrative examples of A in the formula (1c) include the same examples as A in the formula (1).

In the formulae (a) and (b), $R^{100}$, $R^{200}$, $R^{300}$, $R^{400}$ and $R^{500}$ independently represent a heteroatom or a linear monovalent hydrocarbon group having 1 to 20 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom. Two or more of $R^{100}$, $R^{200}$, and $R^{300}$ may be bonded to each other to form a ring together with the sulfur atom in the formula. Illustrative examples of $R^{100}$, $R^{200}$, $R^{300}$, $R^{400}$ and $R^{500}$ include a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, an oxanorbornyl group, a tricyclo[5.2.1.0$^{2,6}$]decanyl group, an adamantyl group, a phenyl group, a naphthyl group, and an anthracenyl group. Moreover, a part of hydrogen atoms in these groups may be substituted with a group containing a heteroatom such as an oxygen atom, a sulfur atom, a nitrogen atom, and a halogen atom, or a heteroatom such as an oxygen atom, a sulfur atom, and a nitrogen atom may be partially inserted between carbon atoms so as to form a hydroxyl group, a cyano group, a carbonyl group, an ether bond, an ester bond, a sulfonate ester bond, a carbonate bond, a lactone ring, a sultone ring, a carboxylic anhydride, a haloalkyl group or the like.

Illustrative examples of the cation structure $M_b^+$ in the formula (1c) are shown below.

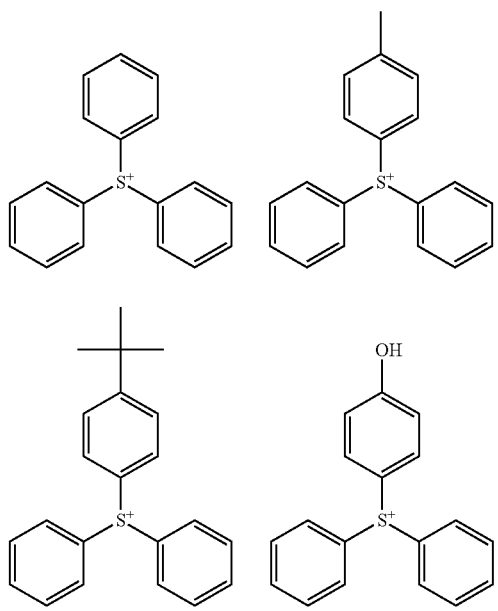

-continued
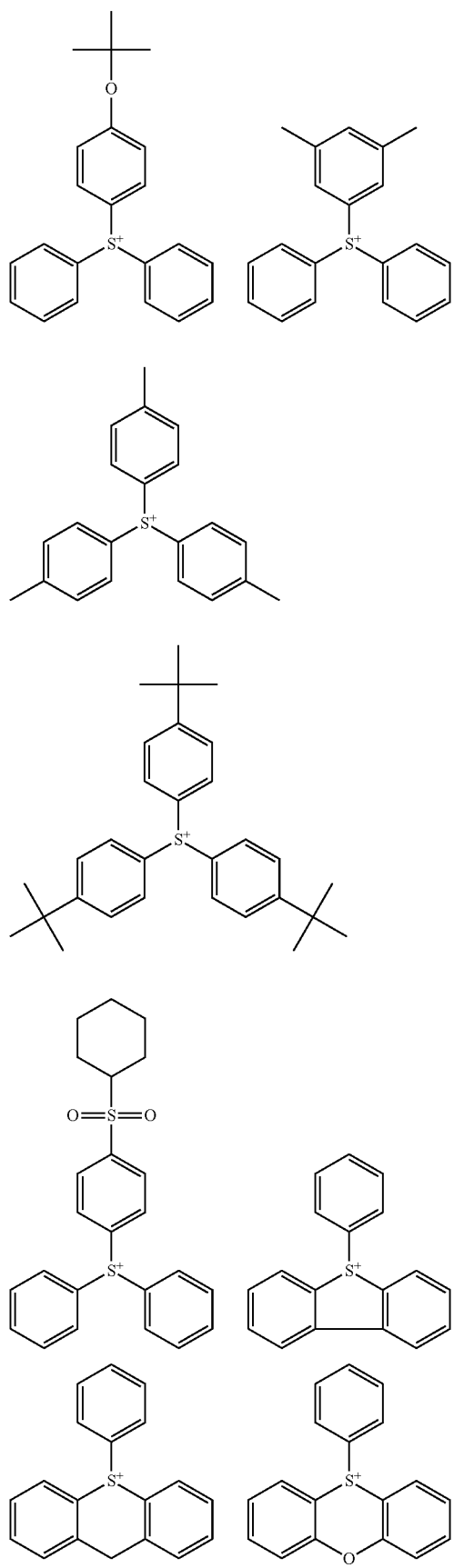
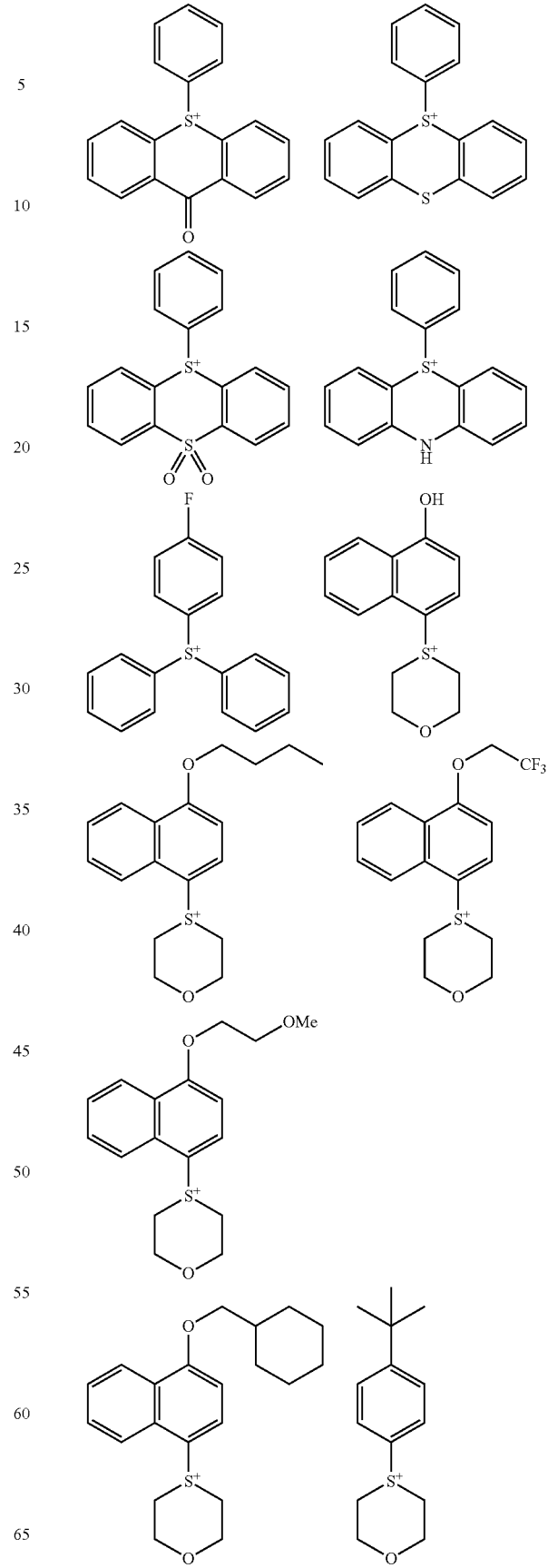

-continued

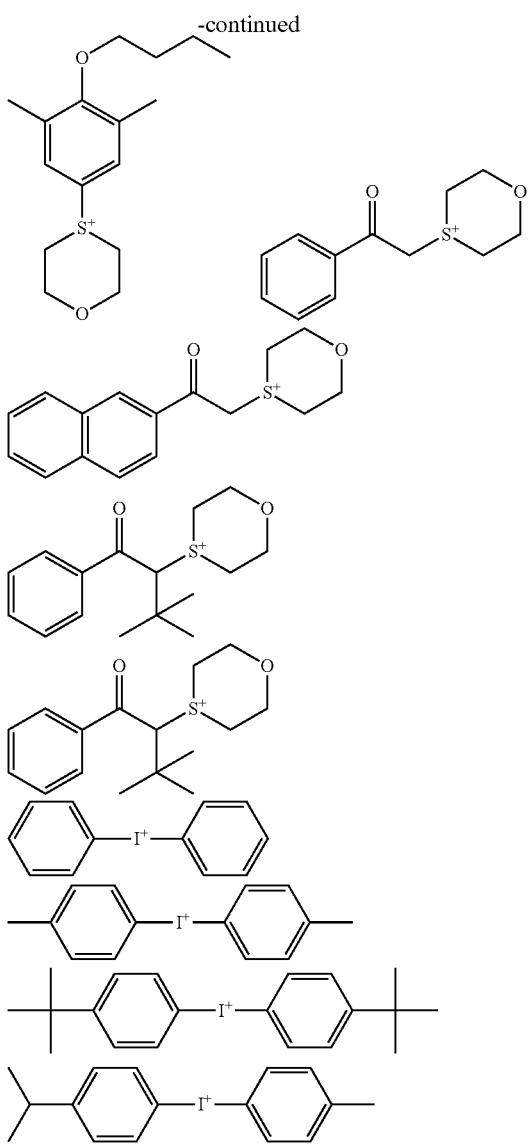

Moreover, the inventive polymer compound containing the repeating unit shown by the formula (1c) may contain the repeating units shown by the formulae (2), (3), (p1), (p2), (d1), and (d2) and repeating units based on other monomers, which are mentioned above as the repeating units that may be contained in the polymer compound that changes into the polymer compound having the sulfonic acid structure shown by the formula (1a).

The inventive polymer compound containing the repeating unit shown by the formula (1c) preferably has a weight average molecular weight of 1,000 to 500,000, more preferably 3,000 to 100,000. When the weight average molecular weight of the polymer compound is in this range, it is possible to prevent an excessive reduction in etching resistance and a reduction in resolution due to lack of dissolution rate difference between before and after exposure. The molecular weight can be measured by gel permeation chromatography (GPO) in terms of polystyrene.

In the inventive polymer compound containing the repeating unit shown by the formula (1c), preferable content ratio (mol %) of each repeating unit is, for example, as shown below, although the ratio is not limited to this range.

The inventive polymer compound containing the repeating unit shown by the formula (1c) preferably contains:

(I) one or more repeating units shown by the formula (1c) in an amount of 1 to 30 mol %, preferably 1 to 20 mol %, more preferably 1 to 10 mol % in total;

(II) one or more repeating units shown by the formula (2) or (3) in an amount of 1 mol % or more and 60 mol % or less, preferably 5 to 50 mol %, more preferably 10 to 50 mol % in total;

(III) one or more repeating units shown by the formula (p1) or (p2) in an amount of 0 mol % or more and 60 mol % or less, preferably 5 to 50 mol %, more preferably 10 to 50 mol % in total, as needed;

(IV) one or more repeating units shown by the formula (d1) or (d2) in an amount of 0 to 30 mol %, preferably 0 to 20 mol %, more preferably 0 to 10 mol % in total, as needed; and (V) one or more repeating units based on other monomers in an amount of 0 to 80 mol %, preferably 0 to 70 mol %, more preferably 0 to 50 mol % in total, as needed.

The repeating unit shown by the formula (1c) allows various structural design by variously combining A in the anion structure and the cation $M_b^+$. Thus, this repeating unit allows an appropriate structural design according to use and change of the wavelength of exposure light, other copolymerization units in the base resin, and a casting solvent in the resist composition.

The polymer compound containing the repeating unit shown by the formula (1c) can be synthesized by, for example, adding a radical polymerization initiator to a compound shown by the formula (1) in which $M^+=M_b^+$ in an organic solvent to initiate radical polymerization. If necessary, compounds for forming other repeating units may be added thereto for the radical polymerization.

The radical polymerization may be conducted, for example, in the same manner as the method for synthesizing the polymer compound containing the repeating unit shown by the formula (1b).

The polymerization initiator used in the polymerization may be, for example, the same as used for synthesizing the polymer compound containing the repeating unit shown by the formula (1b). The heating temperature and the reaction time may be also the same as in the method for synthesizing the polymer compound containing the repeating unit shown by the formula (1b).

Alternatively, the polymer compound containing the repeating unit shown by the formula (1c) can be synthesized by the following reaction.

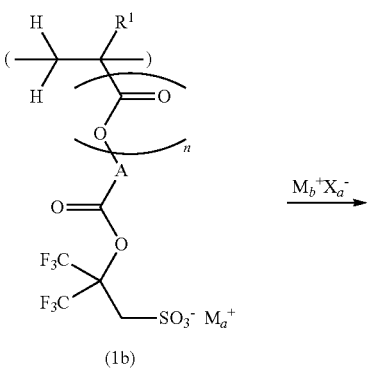

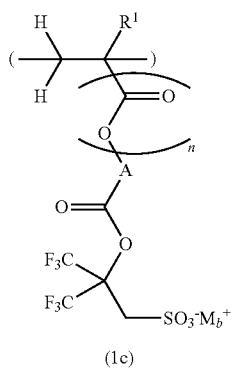

(1c)

wherein $R^1$, A, "n", $M_a^+$, $M_b^+$ and $X_a^-$ are as defined above.

The polymer compound containing the repeating unit shown by the formula (1c) can be produced by ion-exchange reaction of the polymer compound containing the repeating unit shown by the formula (1b). Meanwhile, the ion-exchange reaction is elaborated in Japanese Patent Laid-Open Publication No. 2007-145797, for example.

The inventive polymer compound as described above can provide a resist composition that has high resolution and high sensitivity and is excellent in balance of lithography properties such as LWR and CDU when used as a base resin of the resist composition.

<Resist Composition>

Furthermore, the present invention provides a resist composition containing (A) the above polymer compound and (B) an organic solvent.

More specifically, the inventive resist composition contains:
(A) a base resin; and
(B) an organic solvent; and may further contain:
(C) a photo acid generator capable of generating an acid other than the sulfonic acid structure shown by the formula (1a);
(D) a nitrogen-containing compound; and
(E) a surfactant that is insoluble or difficultly soluble in water and soluble in an alkaline developer and/or a surfactant (a hydrophobic resin) that is insoluble or difficultly soluble in water and an alkaline developer, if necessary.

[(A) Base Resin]

The base resin may be the polymer compound that changes into the polymer compound having the sulfonic acid structure shown by the formula (1a) or may be the polymer compound containing the repeating unit shown by the formula (1b) or (1c), which function as a photo acid generator.

[(B) Organic Solvent]

The component (B), an organic solvent, contained in the inventive resist composition may be any organic solvent that can dissolve the inventive polymer compound, a photo acid generator, a nitrogen-containing compound, and other additives described later. Illustrative examples of the organic solvent include ketones such as cyclohexanone and methyl-2-n-amyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone; and a mixed solvent thereof. When an acetal type acid-labile group is used, an alcohol solvent with high boiling point, such as diethylene glycol, propylene glycol, glycerin, 1,4-butanediol, and 1,3-butanediol, may be added to accelerate the deprotection reaction of the acetal.

Among these organic solvents, 1-ethoxy-2-propanol, propylene glycol monomethyl ether acetate, cyclohexanone, γ-butyrolactone, and a mixed solvent thereof, which are particularly excellent in solubility with respect to the photo acid generator in the resist component, are preferably used in the present invention. The amount of the organic solvent to be used is preferably 200 to 7,000 parts by mass, particularly preferably 400 to 5,000 parts by mass, based on 100 parts by mass of the base resin in the resist composition.

[(C) Photo Acid Generator Capable of Generating Acid Other than Sulfonic Acid Structure Shown by Formula (1a)]

The inventive resist composition is characterized by containing the base resin composed of the polymer compound incorporating the repeating unit that functions as a photo acid generator in its molecule. In addition to this, a non-polymer type acid generator may be contained therein to finely adjust lithography properties. The photo acid generator to be used may be any compounds capable of generating an acid by irradiation with a high energy beam. Preferable examples of this additional photo acid generator include a sulfonium salt, iodonium salt, sulfonyldiazomethane, N-sulfonyloxyimide, and oxime-o-sulfonate type acid generator. These acid generators may be used alone or in combination of two or more kinds. An acid generated from the acid generator is most preferably a sulfonic acid. In addition, photo acid generators that have sufficient acidity to cleave an acid-labile group, such as bis(perfluoroalkanesulfonyl)imide and tris(perfluoromethanesulfonyl)methide, are also preferably used.

Such photo acid generator is preferably has a structure shown by the formula (4),

(4)

wherein $M_b^+$ is as defined above; R represents a hydrogen atom or a linear monovalent hydrocarbon group having 1 to 27 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom.

Illustrative examples of R in the formula (4) include a hydrogen atom, a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, an oxanorbornyl group, a tricyclo[5.2.1.0$^{2,6}$]decanyl group, an adamantyl group, a phenyl group, a naphthyl group, and an anthracenyl group. Moreover, a part of hydrogen atoms in these groups may be substituted with a group containing a heteroatom such as an oxygen atom, a sulfur atom, a nitrogen atom, and a halogen atom, or a heteroatom such as an oxygen atom, a sulfur atom, and a nitrogen atom may be partially inserted between carbon atoms so as to form a hydroxyl group, a cyano group, a carbonyl group, an ether bond, an ester bond, a sulfonate ester bond, a carbonate bond, a lactone ring, a sultone ring, a carboxylic anhydride, a haloalkyl group or the like.

In the case of using a tertiary ester or ether protective group for the acid-labile group contained in the inventive polymer compound used as the base resin of the resist composition, the α-position of the sulfo group in the formula (4) is preferably substituted with fluorine. This is because such a protective group is more easily cleaved by a generated acid having stronger acidity. Illustrative examples of the photo acid generator having α,α-difluorosulfonate in the anion structure include compounds described in paragraphs (0122) to (0142) of Japanese Patent Laid-Open Publication No. 2008-111103, compounds described in paragraphs (0088) to (0092) of Japanese Patent Laid-Open Publication No. 2014-001259, compounds described in paragraphs (0015) to (0017) of Japanese Patent Laid-Open Publication No. 2012-41320, and compounds described in paragraphs (0015) to (0029) of Japanese Patent Laid-Open Publication No. 2012-106986.

In the case of using an acetal protective group for the acid-labile group contained in the inventive polymer compound used as the base resin of the resist composition, the α-position of the sulfo group in the formula (4) is preferably substituted with no fluorine. This is because such a photo acid generator, which does not generate a strong acid such as α,α-difluorosulfonic acid, can prevent uncontrollable acid diffusion due to an excessive cleavage of a protective group. Such a photo acid generator may combine a specific anion structure shown below and an appropriate cation structure shown by $M_b^+$ in the formula (4). However, the photo acid generator used in the present invention is not limited thereto.

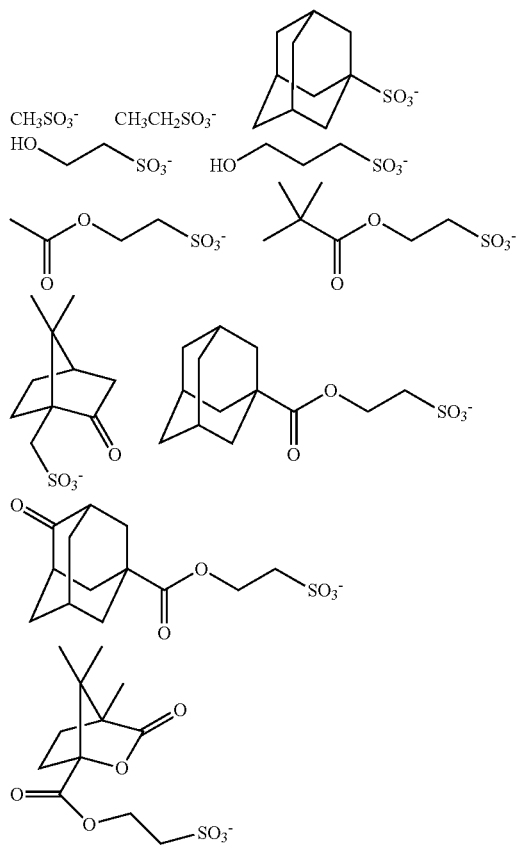

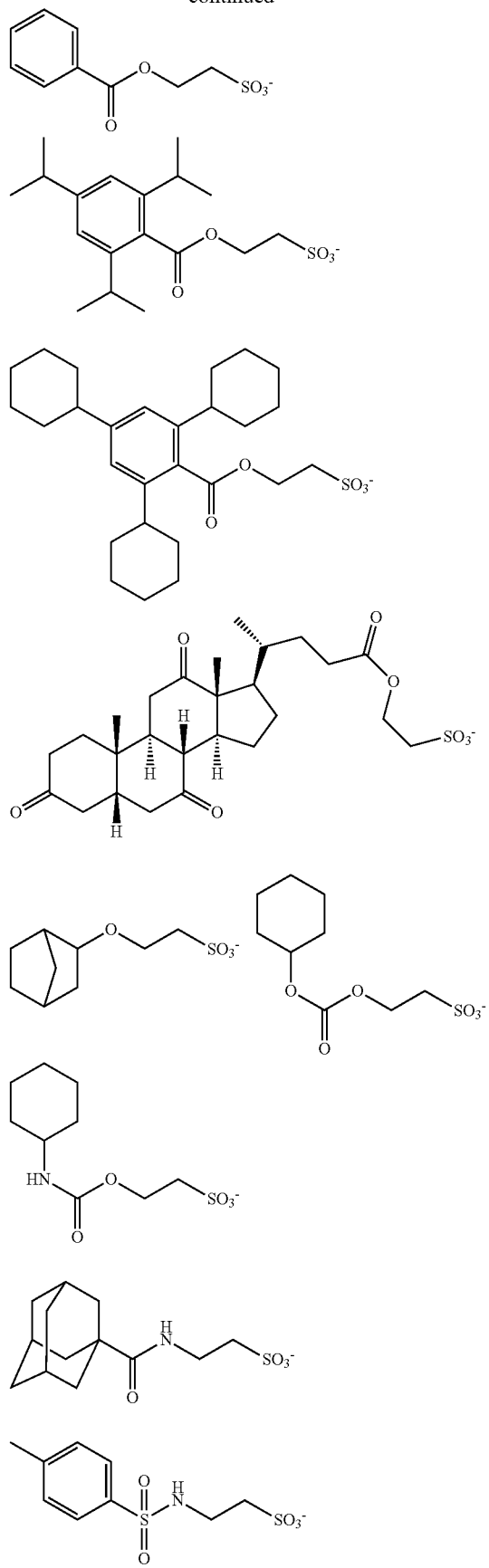

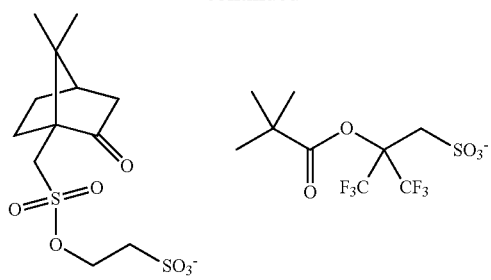
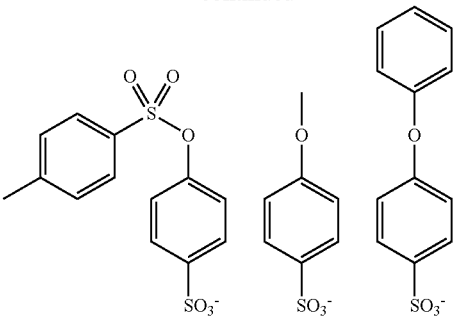
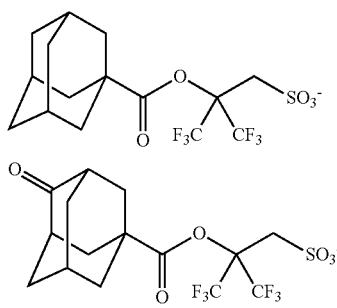
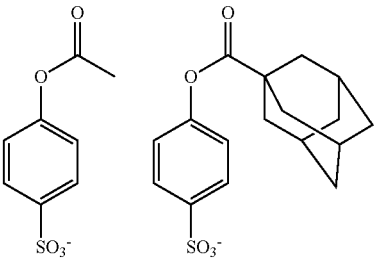
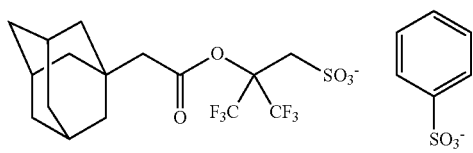
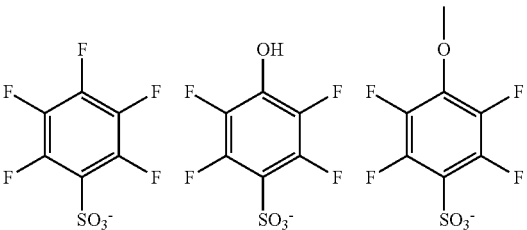
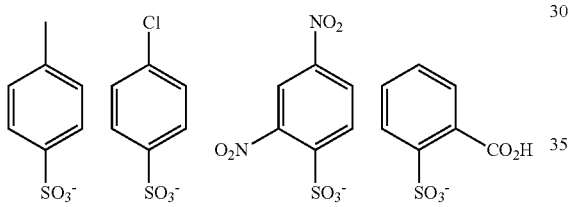
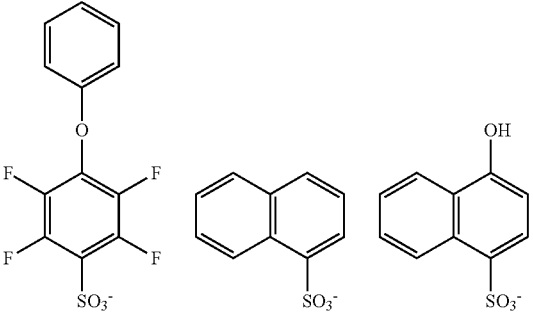
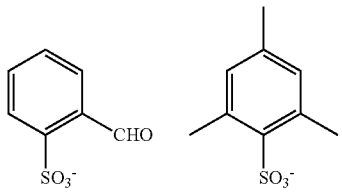
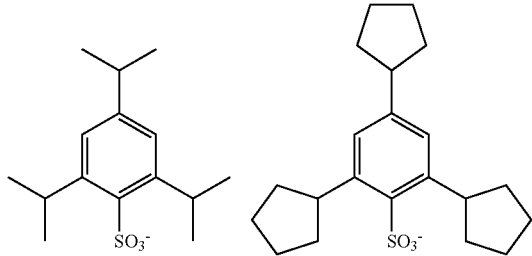
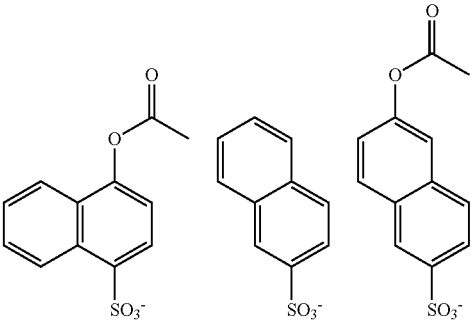
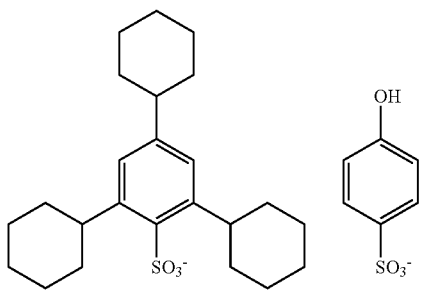
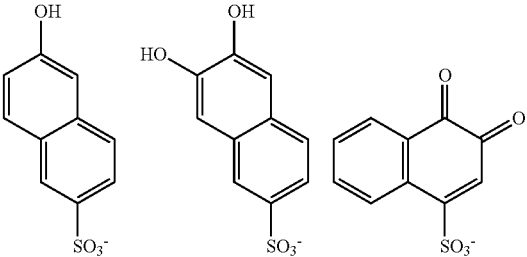

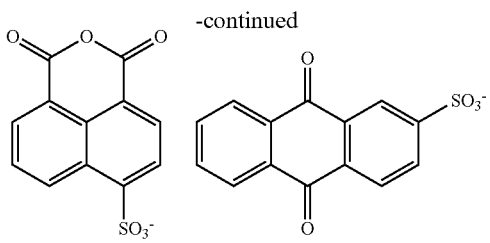

The adding amount of (C) the photo acid generator is preferably 0 to 40 parts by mass, more preferably 0.1 to 40 parts by mass, particularly preferably 0.1 to 20 parts by mass, based on 100 parts by mass of the base resin in the resist composition. When the adding amount of the photo acid generator is in this range, it is possible to prevent the resolution from decreasing due to an excess photo acid generator and foreign matters from occurring after resist development or during resist removal.

[(D) Nitrogen-Containing Compound]

The inventive resist composition may further contain a nitrogen-containing compound as a quencher, if necessary. Herein, the quencher means a compound that can reduce the diffusion rate when an acid generated from the photo acid generator diffuses into a resist film. Illustrative examples of the nitrogen-containing compound preferably used as the quencher are described in paragraphs (0146) to (0164) of Japanese Patent Laid-Open Publication No. 2008-111103, including primary, secondary, or tertiary amine compounds, especially, amine compounds having a hydroxyl group, an ether bond, an ester bond, a lactone ring, a cyano group, or a sulfonate ester bond. As other examples, there may be mentioned compounds in which a primary or secondary amine is protected by forming a carbamate group, as disclosed in Japanese Patent No. 3790649. Such an amine compound having a protected amino group is effective in the case that the resist composition contains an unstable component against a base.

The nitrogen-containing compound may be one kind alone or a combination of two or more kinds. The formulation amount thereof is preferably 0.001 to 12 parts by mass, more preferably 0.01 to 8 parts by mass, based on 100 parts by mass of the base resin. The addition of the nitrogen-containing compound allows easy adjustment of resist sensitivity, improves resolution by reducing the acid diffusion rate in the resist film, and reduces the change of sensitivity after exposure. In addition, this allows a reduction in dependency on substrate or environment, thus improving various properties such as exposure margin, pattern profile, and substrate adhesion.

Furthermore, the inventive resist composition may contain, in addition to the nitrogen-containing compound, a photo-decomposable onium salt having a nitrogen-containing substituent as a quencher, if necessary. Such a compound functions as a quencher at the unexposed part and loses the quencher function at the exposed part by neutralization with an acid generated from itself, which is a so-called photo-degradable base. The photo-degradable base can enhance the contrast between the exposed part and the unexposed part. Illustrative example of the usable photo-degradable base are described, in for example, Japanese Patent Laid-Open Publication No. 2009-109595, No. 2012-46501, and No. 2013-209360.

The adding amount of the photo-decomposable onium salt having a nitrogen-containing substituent is preferably 0 to 40 parts by mass, more preferably 0.1 to 40 parts by mass, particularly preferably 0.1 to 20 parts by mass, based on 100 parts by mass of the base resin in the resist composition. When the adding amount of the photo-decomposable onium salt is in this range, it is possible to prevent the resolution from decreasing due to an excess photo-decomposable onium salt having a nitrogen-containing substituent and foreign matters from occurring after resist development or during resist removal.

[(E) Surfactant that is Insoluble or Difficultly Soluble in Water and Soluble in Alkaline Developer and/or Surfactant (Hydrophobic Resin) that is Insoluble or Difficultly Soluble in Water and Alkaline Developer]

The inventive resist composition may contain (E) a surfactant, for example, as described in paragraph (0166) of Japanese Patent Laid-Open Publication No. 2008-111103. As the surfactant insoluble or difficultly soluble in water and an alkaline developer, FC-4430 available from Sumitomo 3M Ltd., Surflon S-381 available from Seimi Chemical Co., Ltd., surfactants disclosed in the above publication, especially, KH-20 and KH-30 available from Asahi Glass Co., Ltd., and Surfynol E1004 available from Nisshin Chemical Industry Co., Ltd., are preferably used. In addition, oxetane ring-opening polymers shown by the formula (surf-1) is also preferable. These surfactant may be used alone or in combination of two or more kinds.

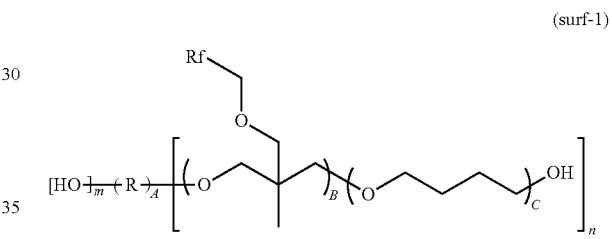

(surf-1)

Here, R, Rf, A, B, C, "m" and "n" are applied only to the formula (surf-1), irrespective of the above description. R represents a 2- to 4-valent aliphatic group having 2 to 5 carbon atoms. Illustrative examples of the divalent group include ethylene, 1,4-butylene, 1,2-propylene, 2,2-dimethyl-1,3-propylene, and 1,5-pentylene; 1,4-butylene and 2,2-dimethyl-1,3-propylene are preferable. Illustrative examples of the trivalent or tetravalent group are shown below. Rf represents a trifluoromethyl group or a pentafluoroethyl group, preferably a trifluoromethyl group. "m" represents an integer of 0 to 3, "n" represents an integer of 1 to 4, and the sum of "m" and "n", which represents the valency of R, is an integer of 2 to 4. A represents 1, B represents an integer of 2 to 25, and C represent an integer of 0 to 10. B is preferably an integer of 4 to 20, and C is preferably 0 or 1. The above structure does not specify the arrangement of the respective constitutional units, and the units may be bonded as a block or randomly.

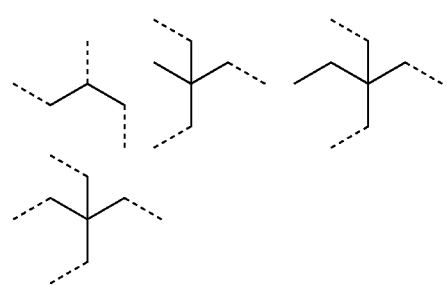

wherein the dotted line represents a bonding arm, and the formulae show partial structures derived from glycerol, trimethylolethane, trimethylolpropane, and pentaerythritol, respectively.

The production of the surfactant of a partially fluorinated oxetane ring-opening polymer type is described in detail in U.S. Pat. No. 5,650,483.

The surfactant insoluble or difficultly soluble in water and soluble in an alkaline developer is put on the resist surface after spin coating and then serves to reduce penetration and leaching of water when a top coat is not used in the ArF immersion exposure. This prevents water-soluble components from eluting from the resist film, thereby reducing damage to an exposure apparatus. In addition, this surfactant is useful in that it is soluble in an alkaline developer at alkali development after post baking and thus hardly becomes a foreign matter which causes defects. The surfactant insoluble or difficultly soluble in water and soluble in an alkaline developer is also referred to as a hydrophobic resin. Above all, surfactants having high water-repellency and capable of improving water-sliding property are preferable. Such a polymer type surfactant are shown below, for example.

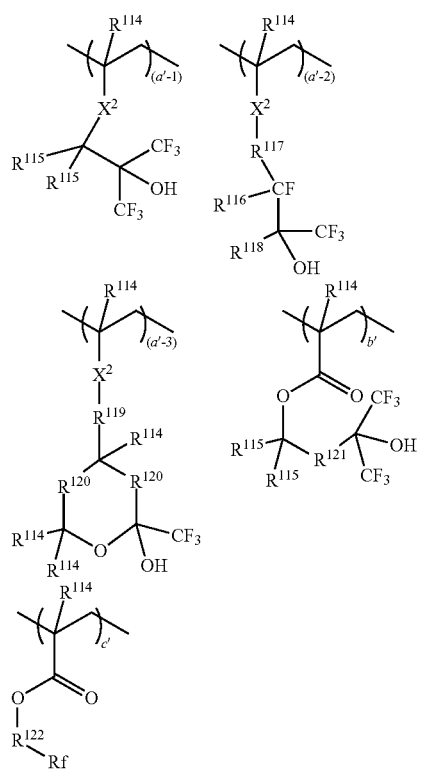

wherein each $R^{114}$ may be the same or different and represents a hydrogen atom, a fluorine atom, a methyl group, or a trifluoromethyl group; each $R^{115}$ may be the same or different and represents a hydrogen atom or a linear, branched, or cyclic alkyl group or fluorinated alkyl group having 1 to 20 carbon atoms, in which $R^{115}$ in the same monomer may be bonded to each other to form a ring together with the carbon atoms to which they are bonded, and in this case, the combination represents a linear, branched, or cyclic alkylene group or a fluorinated alkylene group having 2 to 20 carbon atoms in total; $R^{116}$ represents a fluorine atom or a hydrogen atom or may be bonded to $R^{117}$ to form a non-aromatic ring having 3 to 10 carbon atoms in total together with the carbon atoms to which they are bonded; $R^{117}$ represents a linear, branched, or cyclic alkylene group having 1 to 6 carbon atoms, in which one or more hydrogen atoms may be each substituted with a fluorine atom; $R^{118}$ represents a linear or branched alkyl group having 1 to 10 carbon atoms, in which one or more hydrogen atoms are each substituted with a fluorine atom, or $R^{117}$ and $R^{118}$ may be bonded to each other to form a trivalent non-aromatic organic group having 2 to 12 carbon atoms in total together with the carbon atoms to which they are bonded; $R^{118}$ represents a single bond or an alkylene group having 1 to 4 carbon atoms; each $R^{120}$ may be the same or different and represents a single bond, —O—, or —CR$^{114}$R$^{114}$—; $R^{121}$ represents a linear or branched alkylene group having 1 to 4 carbon atoms or may be bonded to $R^{115}$ in the same monomer to form a non-aromatic ring having 3 to 6 carbon atoms together with the carbon atoms to which they are bonded; $R^{122}$ represents a 1,2-ethylene group, a 1,3-propylene group, or a 1,4-butylene group; Rf represents a linear perfluoroalkyl group having 3 to 6 carbon atoms, a 3H-perfluoropropyl group, a 4H-perfluorobutyl group, a 5H-perfluoropentyl group, or a 6H-perfluorohexyl group; each $X^2$ may be the same or different and represents —C(=O)—O—, —O—, or —C(=O)—R$^{123}$—C(=O)—O—, where $R^{123}$ represents a linear, branched, or cyclic alkylene group having 1 to 10 carbon atoms; and (a'-1), (a'-2), (a'-3), b', and c' satisfy $0 \leq (a'-1) < 1$, $0 \leq (a'-2) < 1$, $0 \leq (a'-3) < 1$, $0 < (a'-1)+(a'-2)+(a'-3) < 1$, $0 \leq b' < 1$, $0 \leq c' < 1$, and $0 < (a'-1)+(a'-2)+(a'-3)+b'+c' \leq 1$.

Examples of a repeating unit of the polymer type surfactant are shown below.

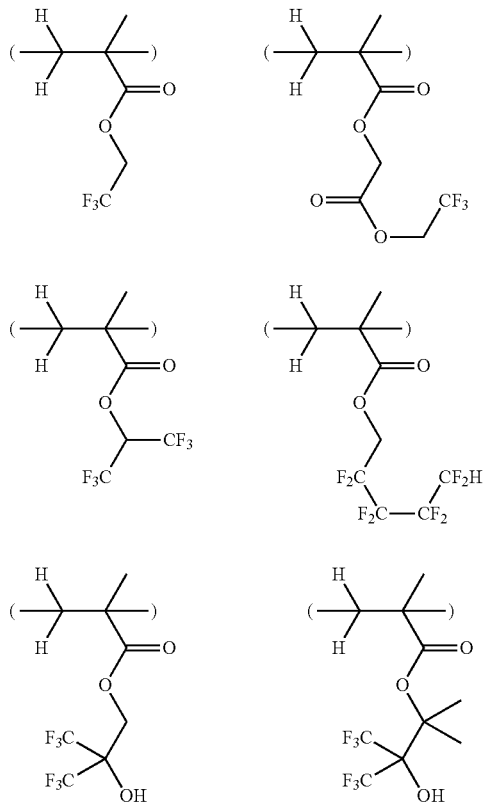

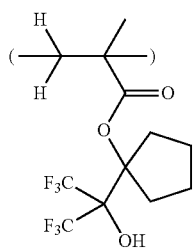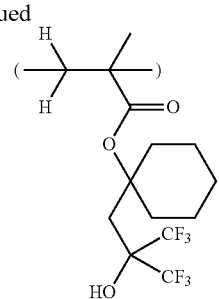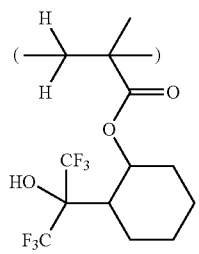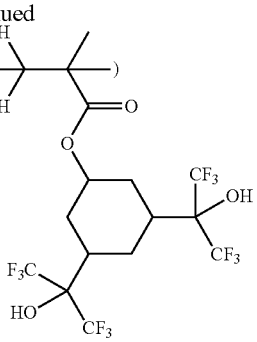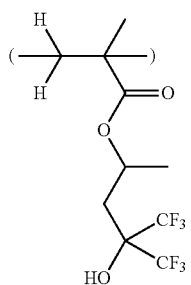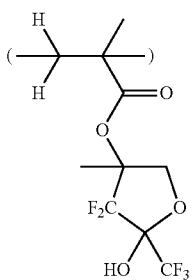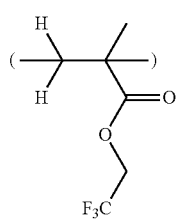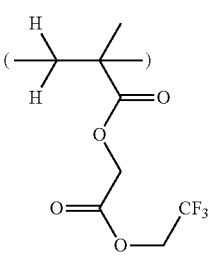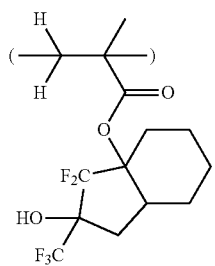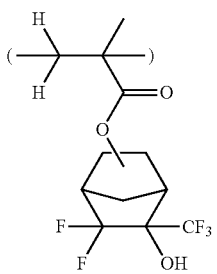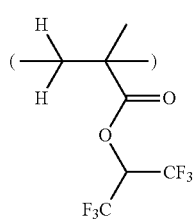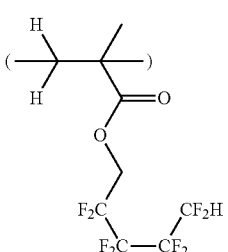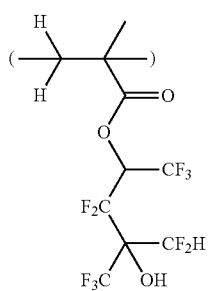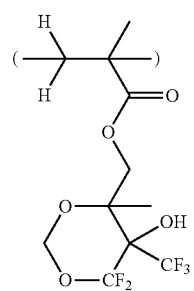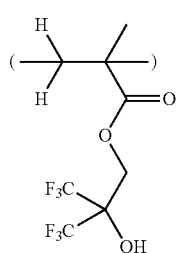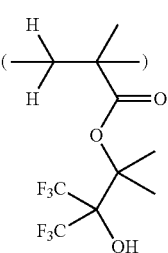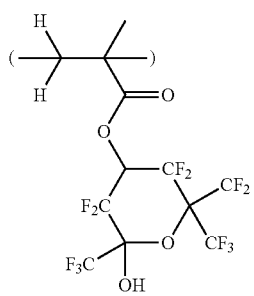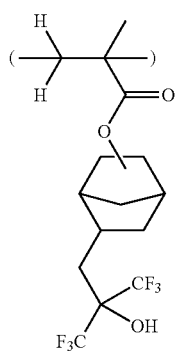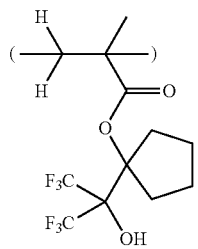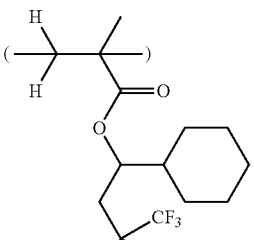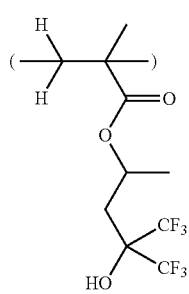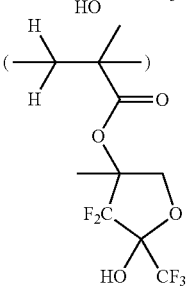

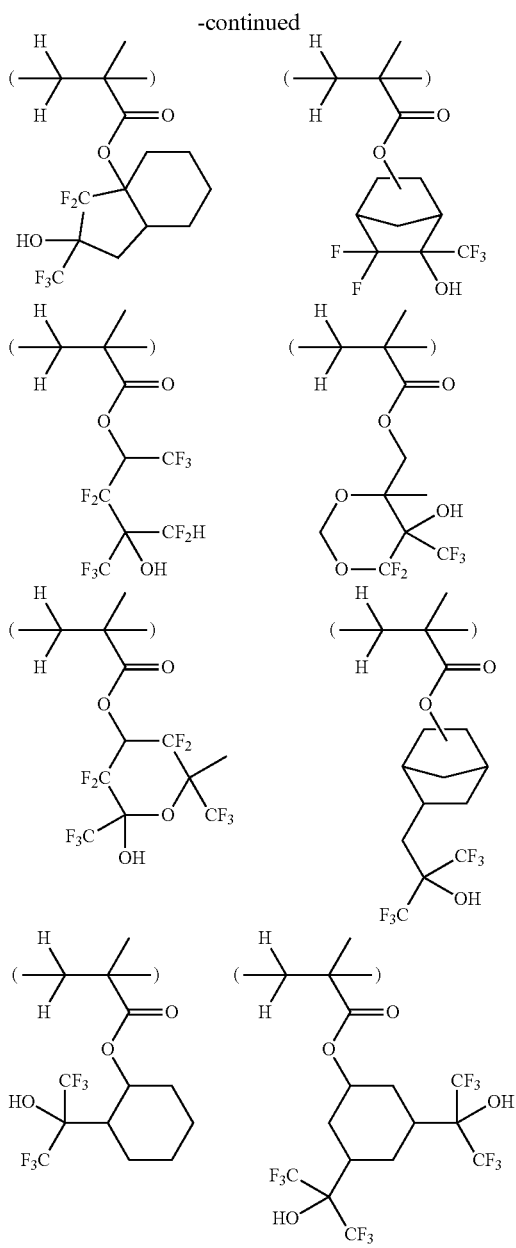

Other examples of the surfactants insoluble or difficultly soluble in water and soluble in an alkaline developer include surfactants described in Japanese Patent Laid-Open Publication No. 2008-122932, No. 2010-134012, No. 2010-107695, No. 2009-276363, No. 2009-192784, No. 2009-191151, No. 2009-98638, No. 2010-250105, and No. 2011-42789.

The polymer type surfactant preferably has a weight average molecular weight of 1,000 to 50,000, more preferably 2,000 to 20,000. This range can prevent insufficient surface modification effect and development failure, and thus is preferable. Herein, the weight average molecular weight is expressed by values measured by gel permeation chromatography (GPC) in terms of polystyrene. The adding amount thereof is preferably 0.001 to 20 parts by mass, more preferably 0.01 to 10 parts by mass, based on 100 parts by mass of the base resin of the resist composition. Japanese Patent Laid-Open Publication No. 2010-215608 describes this surfactant in detail.

The surfactant insoluble in water and soluble in an alkaline developer also can be dissolved in an alcohol solvent having 4 or more carbon atoms, an ether solvent having 8 to 12 carbon atoms, or a mixed solvent thereof.

<Patterning Process>

Furthermore, the present invention provides a patterning process including the steps of: applying the above resist composition on a substrate and baking the resist composition to form a resist film; exposing the formed resist film to a KrF excimer laser beam, an ArF excimer laser beam, an electron beam, or an EUV via a photomask; baking the exposed resist film; and then developing the resist film with a developer.

To form a pattern with the inventive resist composition, a well-known lithography technology may be employed. For example, the resist composition is applied onto a substrate by a procedure such as spin coating so as to give a film thickness of 0.05 to 2.0 μm and then prebaked on a hot plate at 60 to 150° C. for 1 to 10 minutes, preferably at 80 to 140° C. for 1 to 5 minutes to form a resist film. Then, a photomask for forming an intended pattern is placed over the formed resist film, and the film is exposed to a high energy beam. Then, heat treatment (post exposure baking, PEB) is performed on a hot plate at 60 to 150° C. for 1 to 5 minutes, preferably at 80 to 140° C. for 1 to 3 minutes. The film is then developed by a usual method such as dip method, puddle method, and spray method, with a developer for 0.1 to 3 minutes, preferably 0.5 to 2 minutes. The intended pattern can be thus formed on the substrate. The development may be positive tone development, in which the exposed part is developed and dissolved with an alkaline developer such as 0.1 to 5 mass %, preferably 2 to 3 mass % tetramethylammonium hydroxide (TMAH) solution, or may be negative tone development, in which the unexposed part is developed and dissolved with an organic solvent.

[Substrate]

The substrate may be for example, but not particularly limited to, a substrate for manufacturing integrated circuits (e.g. Si, $SiO_2$, SiN, SiON, TiN, WSi, BPSG (Boron Phosphorus Silicate Glass), SOG (Spin on Glass), and an organic antireflection film), or a substrate for manufacturing mask circuits (e.g. Cr, CrO, CrON, and MoSi).

[Exposure]

The exposure may be carried out by a usual exposure method, or an immersion exposure method, in which a liquid is introduced between a resist film and a projection lens. The liquid placed between the resist film and the projection lens preferably has a refractive index of 1.0 or more. In the immersion exposure, a top coat may be applied on the resist film before placing the liquid having a refractive index of 1.0 or more between the top coat and the projection lens to perform the immersion exposure.

(Top Coat)

The top coat is insoluble in water and used for preventing elution from the resist film and enhancing water-sliding property of the film surface. Such a top coat can be classified into two types. One is an organic solvent-removable type, which requires to be removed with an organic solvent that does not dissolve the resist film before alkali development. The other is an alkali-soluble type, which is soluble in an alkaline developer and removed together with the solubilized part of the resist film. The latter is preferably a composition in which a base of a polymer compound especially containing a 1,1,1,3,3,3-hexafluoro-2-propanol residue, which is insoluble in water and soluble in an alkaline developer, is dissolved in an alcohol solvent having 4 or more carbon atoms, an ether solvent having 8 to 12 carbon atoms, or a mixed solvent thereof.

(High Energy Beam)

The high energy beam used in the exposure of the resist film may be for example, but not particularly limited to, a KrE excimer laser beam, an ArF excimer laser beam, an electron beam, or an EUV. The high energy beam is radiated with an exposure dose of preferably 1 to 200 mJ/cm$^2$, more preferably 10 to 100 mJ/cm$^2$.

[Developer]

In the case of the organic solvent development, illustrative examples of the developer include 2-octanone, 2-nonanone, 2-heptanone, 3-heptanone, 4-heptanone, 2-hexanone, 3-hexanone, diisobutylketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, 2-phenylethyl acetate, and a combination thereof.

After the resist film is formed, the acid generator and particles may be washed off from the film surface by rinsing with pure water (post-soaking), and water remaining on the film after exposure may be removed by rinsing (post-soaking).

The inventive patterning process may employ a double patterning method, by which the ArF lithography survives until 32-nm. The double patterning method includes a trench method, in which an underlay is processed into a 1:3 trench pattern by first exposure and etching, and after shifting the position, a 1:3 trench pattern is formed by second exposure to form a 1:1 pattern; and a line method, in which a first underlay is processed into a 1:3 isolated pattern to be left by first exposure and etching, and after shifting the position, a second underlay formed under the first underlay is processed into a 1:3 isolated pattern to be left by second exposure to form a 1:1 pattern having a half pitch.

As described above, the inventive compound is suitable as a raw material of a polymer compound usable for a resist composition that has high resolution and high sensitivity and is excellent in balance of lithography properties such as LWR and CDU. Moreover, the resist composition using the inventive polymer compound as the base resin can form a resist film that has high resolution and high sensitivity and is excellent in balance of lithography properties such as LWR and CDU. Moreover, the inventive patterning process using such a resist composition enables a fine pattern rule in photolithography and is very effective in precise and fine patterning.

EXAMPLES

Hereinafter, the present invention will be specifically described with reference to Examples and Comparative Examples, but the present invention is not limited thereto.
<Synthesis of PAG (Photo Acid Generator) Intermediate>

Example 1-1

An aqueous solution of sodium 3,3,3-trifluoro-2-hydroxy-2-trifluoromethylpropane-1-sulfonate was synthesized in according with a method described in Japanese Patent Laid-Open Publication No. 2010-215608. To 1200 g of this aqueous solution (corresponding to 1 mol of sodium 3,3,3-trifluoro-2-hydroxy-2-trifluoromethylpropane-1-sulfonate) were added 223 g of benzyltrimethylammonium chloride and 2000 g of methylene chloride, the mixture was stirred for 10 minutes, and the organic layer was collected. The collected organic layer was washed with water and concentrated under reduced pressure. To the concentrated residue was added diisopropyl ether for recrystallization, and the precipitated solid was collected and dried under reduced pressure to obtain an intended product, 354 g of benzyltrimethylammonium=3,3,3-trifluoro-2-hydroxy-2-trifluoromethylpropane-1-sulfonate (PAG intermediate 1) as a white solid, with a yield of 86%.

Example 1-2

3-methacryloyloxy-1-adamantanecarbonic acid reacted with oxalyl chloride in a toluene solvent to synthesize carboxylic acid chloride. The resulting carboxylic acid chloride was mixed with methylene chloride to form a 25 mass % solution.

Then, 123 g of PAG intermediate 1, 45 g of triethylamine, 9 g of 4-dimethylamino pyridine, and 600 g of methylene chloride were mixed to prepare a solution, and the aforementioned methylene chloride solution of carboxylic acid chloride was added dropwise to the mixed solution under ice-cooling. After dropwise addition, the mixture was aged at room temperature for 10 hours, followed by adding dilute hydrochloric acid to quench the reaction. Then, the organic layer was collected, washed with water, and concentrated under reduced pressure. To the concentrated residue was added 1500 g of diisopropyl ether for to precipitate a crystal. The obtained crystal was collected by filtration, and dried under reduced pressure to obtain an intended product, 126 g of benzyltrimethylammonium=3,3,3-trifluoro-2-(3-methacryloyloxy-1-adamantanecarbonyloxy)-2-trifluoromethylpropane-1-sulfonate (PAG intermediate 2) as a white crystal, with a yield of 64%.
<Synthesis of PAG>

Example 1-3

66 g of PAG intermediate 2, 41 g of triphenylsulfonium=methylsulfate, 400 g of methylene chloride, and 200 g of pure water were mixed to prepare a solution, and the mixed solution was stirred at room temperature for 30 minutes. Then, the organic layer was collected, washed with water, and concentrated under reduced pressure, and 300 g of methyl isobutyl ketone was added thereto. This mixture was washed with water again and concentrated under reduced pressure. The concentrated residue was then washed with diisopropyl ether to obtain 72 g of triphenylsulfonium=3,3,3-trifluoro-2-(3-methacryloyloxy-1-adamantanecarbonyloxy)-2-trifluoromethylpropane-1-sulfonate (PAG Monomer 1) with a yield of 93%.

PAG Monomer1

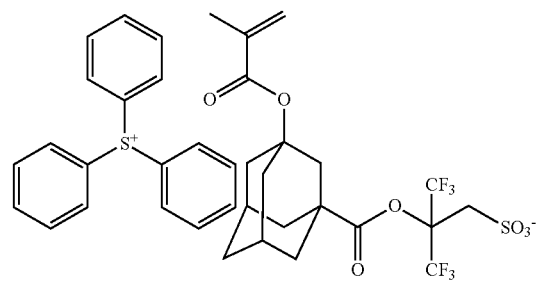

Figure 2:
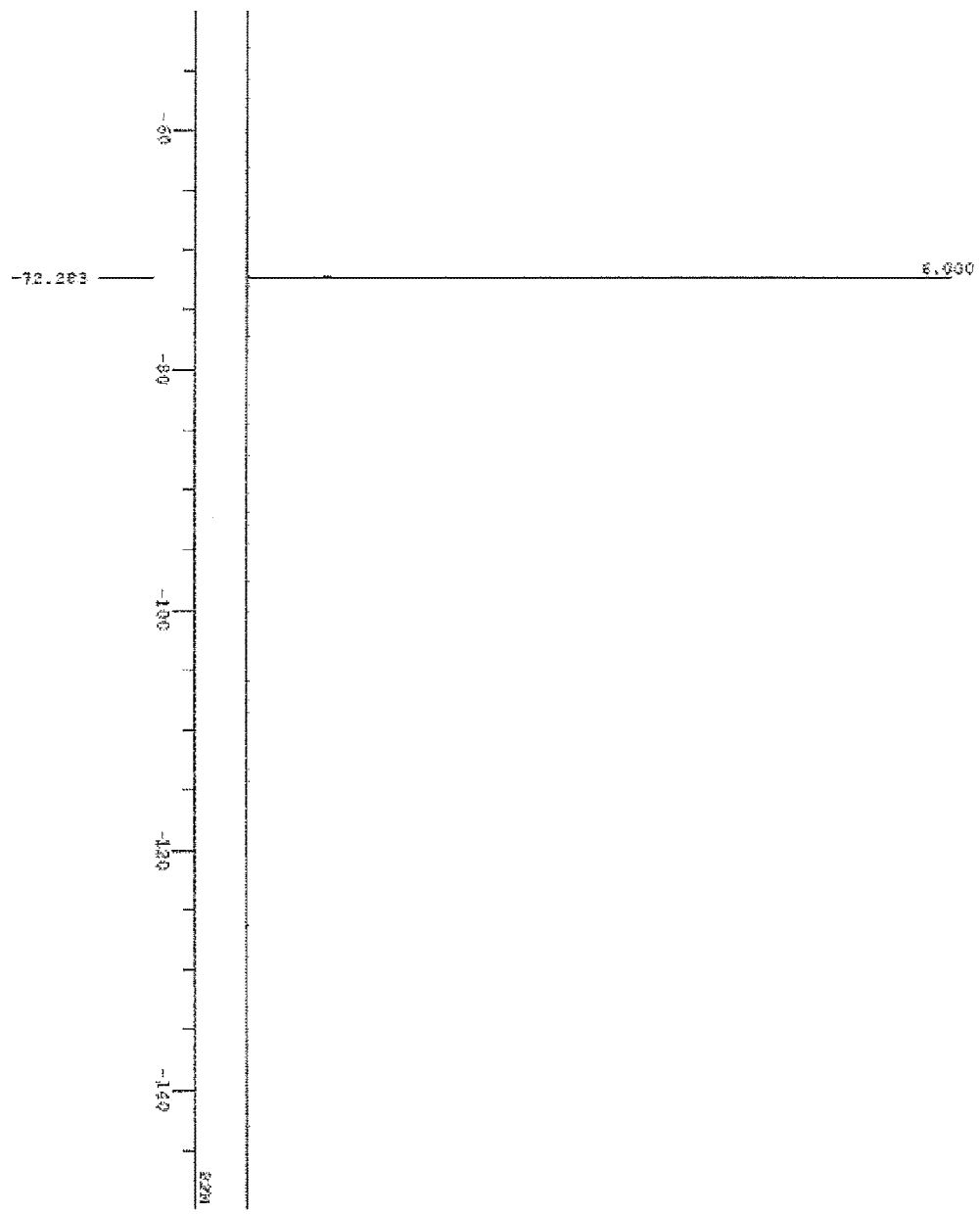
FIG. 2 is a diagram showing $^{19}$F-NMR/DMSO-$d_6$ of PAG Monomer 1 synthesized in Example 1-3.

The spectrum data of PAG Monomer 1 thus obtained are shown below. The results of nuclear magnetic resonance spectrum ($^1$H-NMR, $^{19}$F-NMR/DMSO-d6) are shown in FIG. 1 and FIG. 2. Meanwhile, a trace of residual solvent (diisopropyl ether, methylene chloride, and methyl isobutyl ketone) and water in DMSO-$d_6$ were observed in $^1$H-NMR.

Time-of-Flight mass spectrometry (TOFMS; MALDI)
POSITIVE M$^+$263 (corresponding to $C_{18}H_{15}S^+$)
NEGATIVE M$^-$507 (corresponding to $(C_{14}H_{19}O_2COO)-C(CF_3)_2-CH_2SO_3^-$)

Example 1-4

6.5 g of PAG intermediate 2, 3.1 g of 10-phenyl phenoxathiinium chloride, 50 g of methylene chloride, and 40 g of pure water were mixed to prepare a solution, and the mixed solution was stirred at room temperature for 30 minutes. Then, the organic layer was collected, washed with water, and concentrated under reduced pressure, and 50 g of methyl isobutyl ketone was added thereto. This mixture was washed with water again and concentrated under reduced pressure. The concentrated residue was then washed with diisopropyl ether to obtain 6.9 g of 10-phenyl phenoxathiinium-3,3,3-trifluoro-2-(3-methacryloyloxy-1-adamantanecarbonyloxy)-2-trifluoromethylpropane-1-sulfonate (PAG Monomer 2) with a yield of 88%.

PAG Monomer2

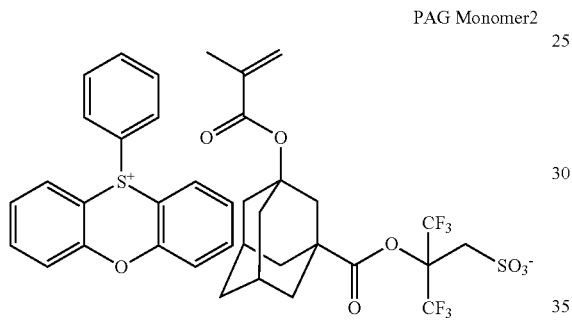

Figure 3:
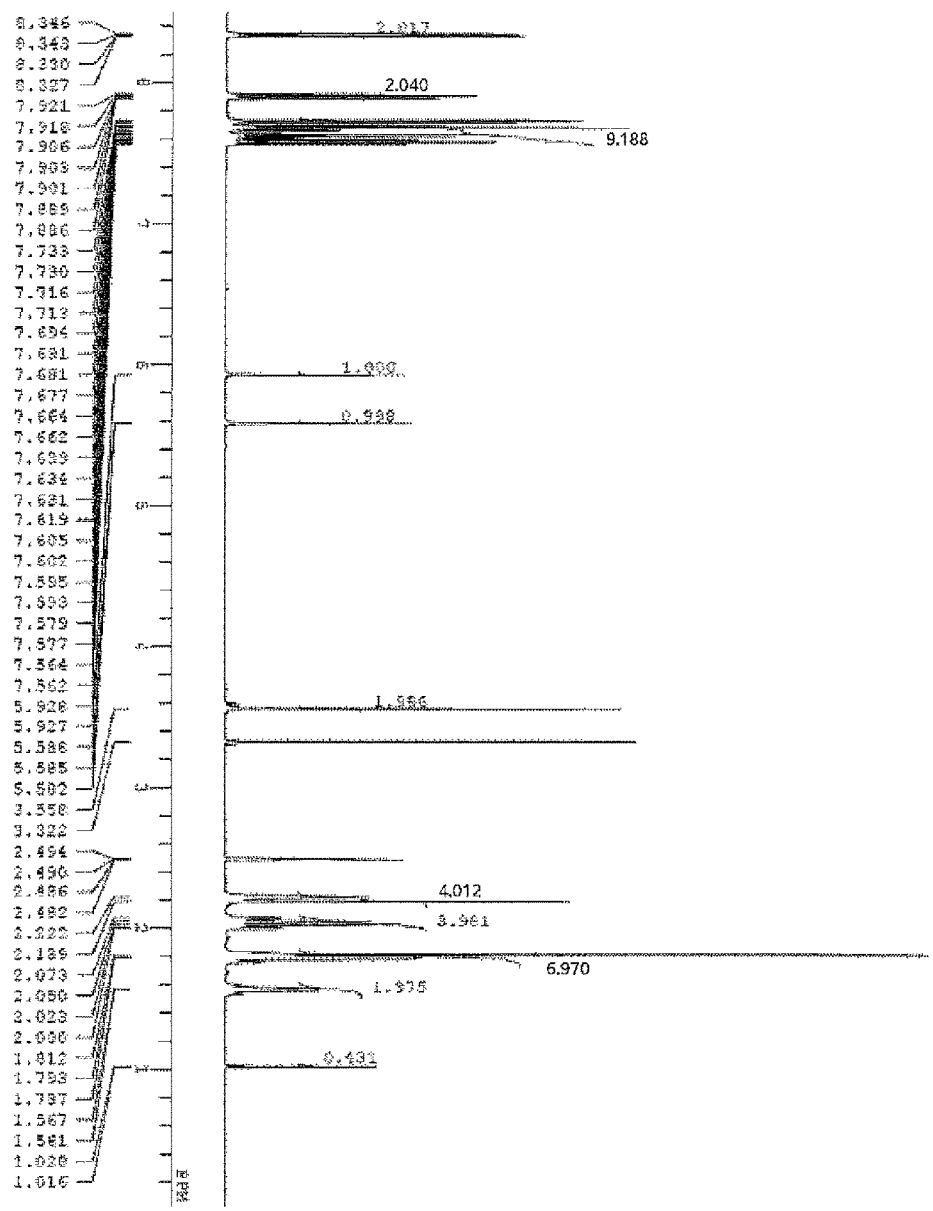
FIG. 3 is a diagram showing $^1$H-NMR/DMSO-$d_6$ of PAG Monomer 2 synthesized in Example 1-4.
Figure 4:
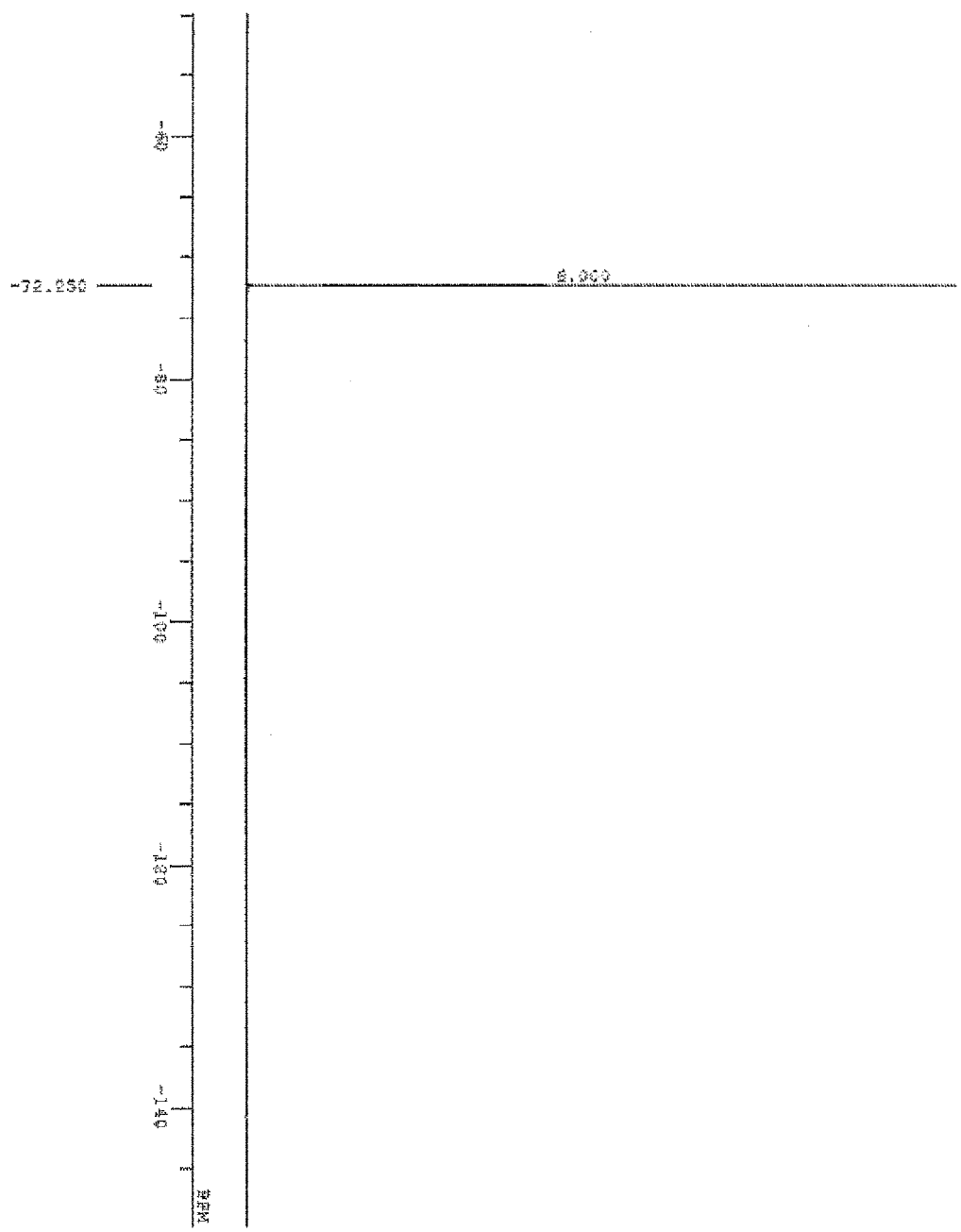
FIG. 4 is a diagram showing $^{19}$F-NMR/DMSO-$d_6$ of PAG Monomer 2 synthesized in Example 1-4.

The spectrum data of PAG Monomer 2 thus obtained are shown below. The results of nuclear magnetic resonance spectrum ($^1$H-NMR, $^{19}$F-NMR/DMSO-$d_6$) are shown in FIG. 3 and FIG. 4. Meanwhile, a trace of residual solvent (diisopropyl ether) and water in DMSO-$d_6$ were observed in $^1$H-NMR.

Infrared absorption spectrum (D-ATR; cm$^{-1}$) 2918, 1760, 1715, 1461, 1441, 1330, 1272, 1238, 1220, 1197, 1166, 1128, 1072, 1041, 1029, 970, 884, 841, 768, 758, 616, 594 cm$^{-1}$ Time-of-Flight mass spectrometry (TOFMS; MALDI)
POSITIVE M$^+$277 (corresponding to $C_{18}H_{13}OS^+$)
NEGATIVE M$^-$507 (corresponding to $(C_{14}H_{19}O_2COO)-C(CF_3)_2-CH_2SO_3^-$)

Comparative Examples 1-1 to 1-4

The following polymerizable group-containing photo acid generators, PAG Monomer 3 to PAG Monomer 6, were synthesized as Comparative Examples.
PAG Monomer 3: a compound described in paragraph (0199) of Japanese Patent Laid-Open Publication No. 2010-077404
PAG Monomer 4: a compound synthesized with reference to paragraph (0199) of Japanese Patent Laid-Open Publication No. 2010-077404
PAG Monomer 5: a compound described in Japanese Patent Laid-Open Publication No. 2010-164963
PAG Monomer 6: a compound synthesized with reference to paragraph (0062) of WO2007/069640 and paragraphs (0218) and (0219) of Japanese Patent Laid-Open Publication No. 2010-215608

(PAG Monomer3)

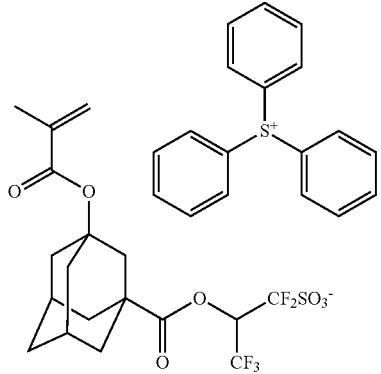

(PAG Monomer4)

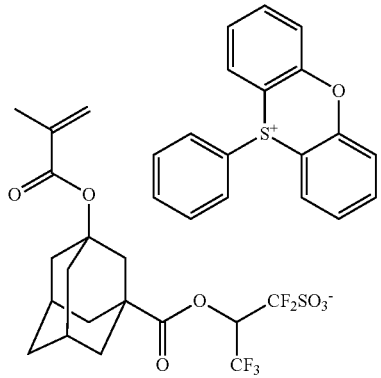

(PAG Monomer5)

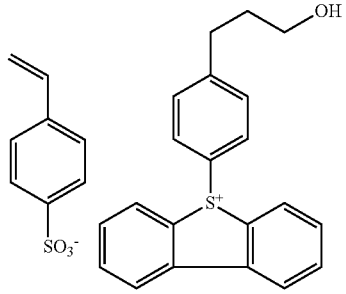

(PAG Monomer6)

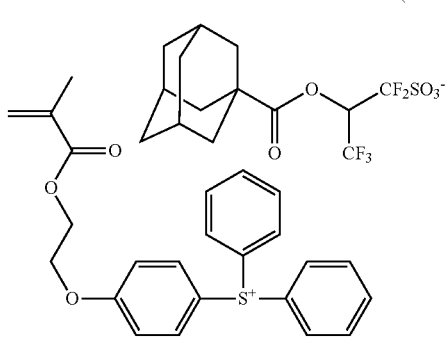

<Synthesis of Polymer Compound>

Example 2-1

A flask under nitrogen atmosphere was charged with 46.0 g of PAG Monomer 2, 24.1 g of 3-ethyl-3-exo-tetracyclo[4.4.0.1$^{2,5}$.1$^{7,10}$]dodecyl methacrylate, 10.4 g of 4-hydroxyphenyl methacrylate, 19.7 g of 4,8-dioxatricyclo[4.2.1.0$^{3,7}$]nonan-5-one-2-yl methacrylate, 19.7 g of dimethyl 2,2'- azobis(isobutyrate), 0.69 g of 2-mercaptoethanol, and 175 g of methyl ethyl ketone (MEK) to prepare a monomer solution. An another flask under nitrogen atmosphere was charged with 58 g of MEK and heated to 80° C. under stirring, and the monomer solution was added dropwise thereto over 4 hours. After completion of dropwise addition, the polymerization solution was continuously stirred for 2 hours with the temperature being maintained at 80° C., and then the solution was cooled to room temperature. The obtained polymerization solution was added dropwise to a mixed solvent of 100 g of MEK and 900 g of hexane, and the precipitated copolymer was collected by filtration. The copolymer was washed with 600 g of hexane twice and then dried under vacuum at 50° C. for 20 hours to obtain 92.1 g of a white powder-like copolymer compound shown by the formula (P-1), with a yield of 92%.

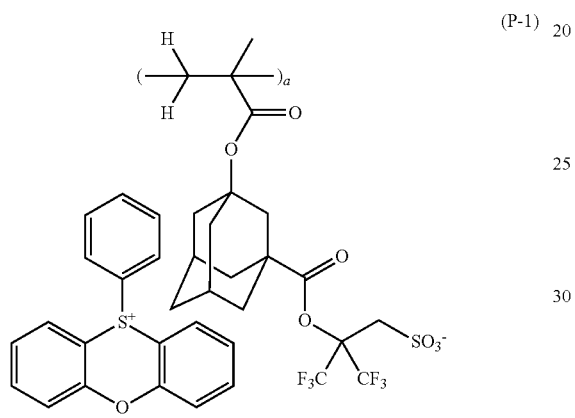

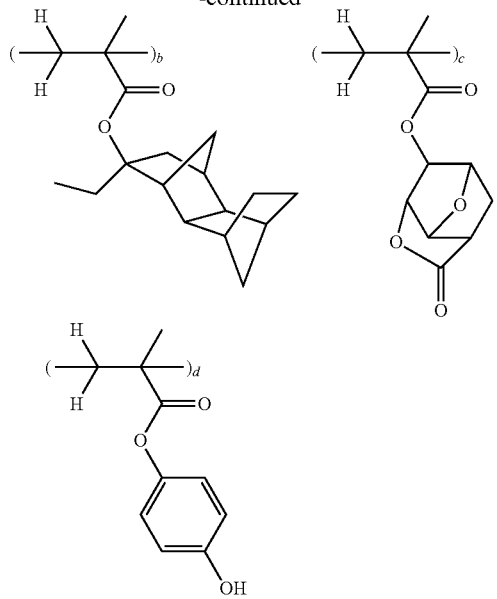

$a = 0.20, b = 0.30, c = 0.30, d = 0.20$

Examples 2-2 to 2-8 and Comparative Examples 2-1 to 2-6

Polymer compounds having structures shown in Table 1 were produced in the same manner as in Example 2-1 except for changing the type and the blending ratio of monomers. Tables 2 to 4 show structures of the repeating units. In Table 1, the inducing ratio means a mole ratio of the introduced repeating unit.

TABLE 1

|  | Polymer compound | Unit1 (introducing ratio) | | Unit2 (introducing ratio) | | Unit3 (introducing ratio) | | Unit4 (introducing ratio) | | Unit5 (introducing ratio) | |
|---|---|---|---|---|---|---|---|---|---|---|---|
| Example 2-1 | P-1 | PAG Unit-2 | (0.20) | A-1 | (0.30) | B-1 | (0.20) | B-4 | (0.30) | — | |
| Example 2-2 | P-2 | PAG Unit-2 | (0.20) | A-1 | (0.20) | A-4 | (0.20) | B-1 | (0.20) | B-4 | (0.20) |
| Example 2-3 | P-3 | PAG Unit-2 | (0.20) | A-1 | (0.20) | A-5 | (0.20) | B-1 | (0.20) | B-4 | (0.20) |
| Example 2-4 | P-4 | PAG Unit-2 | (0.20) | A-1 | (0.20) | A-6 | (0.20) | B-1 | (0.20) | B-4 | (0.20) |
| Example 2-5 | P-5 | PAG Unit-2 | (0.20) | A-3 | (0.30) | B-1 | (0.20) | B-4 | (0.30) | — | |
| Example 2-6 | P-6 | PAG Unit-1 | (0.20) | A-1 | (0.30) | B-2 | (0.10) | B-4 | (0.40) | — | |
| Example 2-7 | P-7 | PAG Unit-1 | (0.20) | A-1 | (0.30) | B-2 | (0.10) | B-3 | (0.40) | — | |
| Example 2-8 | P-8 | PAG Unit-1 | (0.20) | A-3 | (0.30) | B-2 | (0.10) | B-4 | (0.40) | — | |
| Comparative Example 2-1 | P-9 | PAG Unit-4 | (0.20) | A-1 | (0.20) | A-4 | (0.20) | B-1 | (0.20) | B-4 | (0.20) |
| Comparative Example 2-2 | P-10 | PAG Unit-5 | (0.05) | A-1 | (0.30) | A-4 | (0.25) | B-1 | (0.20) | B-4 | (0.20) |
| Comparative Example 2-3 | P-11 | PAG Unit-3 | (0.20) | A-1 | (0.30) | B-2 | (0.10) | B-4 | (0.40) | — | |
| Comparative Example 2-4 | P-12 | PAG Unit-6 | (0.20) | A-1 | (0.20) | A-4 | (0.20) | B-1 | (0.20) | B-4 | (0.20) |
| Comparative Example 2-5 | P-13 | A-1 | (0.30) | A-4 | (0.20) | B-1 | (0.30) | B-4 | (0.20) | — | |
| Comparative Example 2-6 | P-14 | A-1 | (0.40) | B-2 | (0.10) | B-4 | (0.50) | — | | — | |

TABLE 2
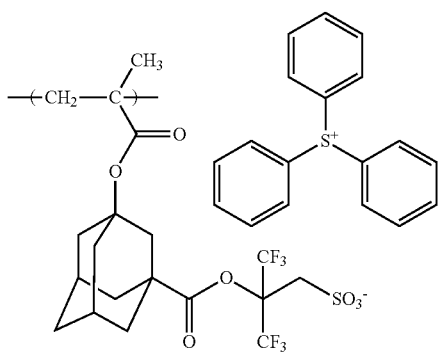 PAG Unit-1
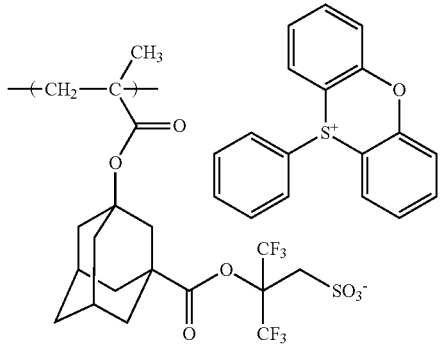 PAG Unit-2
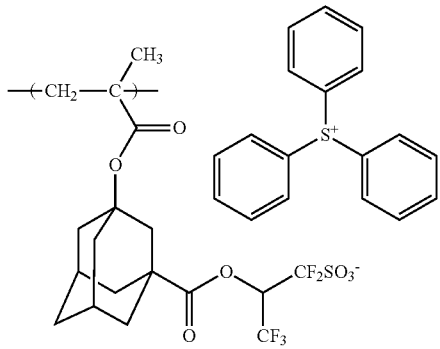 PAG Unit-3
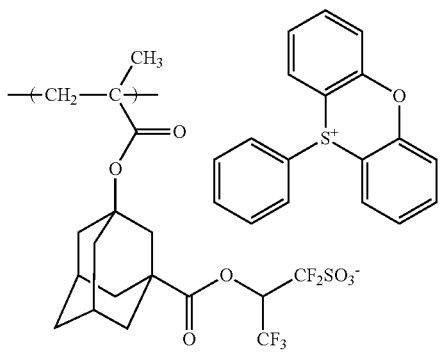 PAG Unit-4
TABLE 2-continued
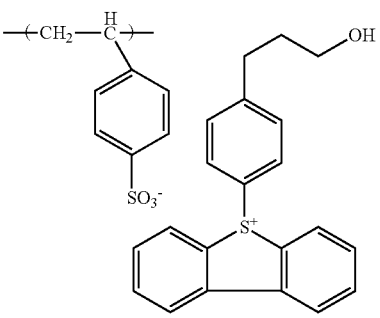 PAG Unit-5
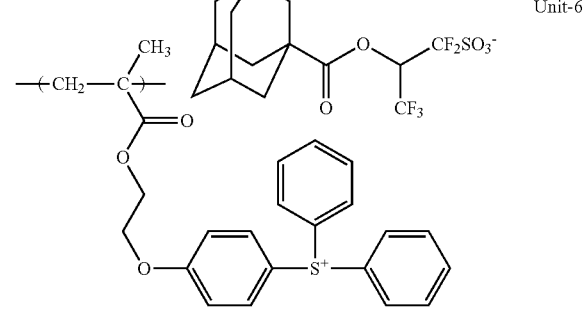 PAG Unit-6
TABLE 3
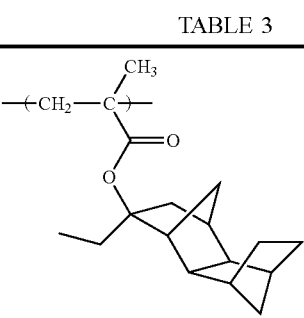 A-1
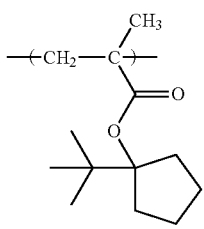 [SMILES: CCC(C)(C)C(=O)OC1(C(C)(C)C)CCCC1] A-2
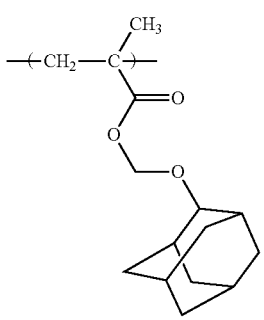 [SMILES: CCC(C)(C)C(=O)OCOC1C2CC3CC(C2)CC1C3] A-3

TABLE 3-continued

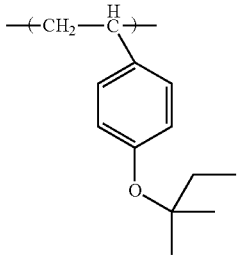 [SMILES: CCC(C)c1ccc(OC(C)(C)CC)cc1] A-4

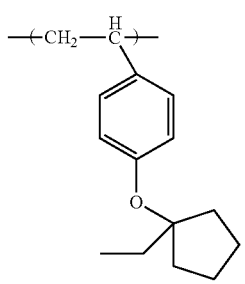 [SMILES: CCC(C)c1ccc(OC2(CC)CCCC2)cc1] A-5

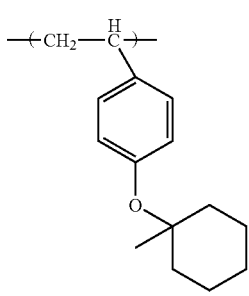 [SMILES: CCC(C)c1ccc(OC2(C)CCCCC2)cc1] A-6

TABLE 4

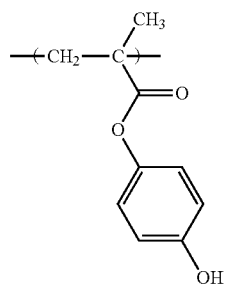 B-1

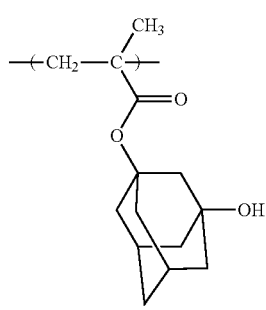 [SMILES: CCC(C)(C)C(=O)OC12CC3CC(CC(O)(C3)C1)C2] B-2

TABLE 4-continued

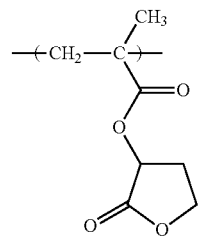 B-3

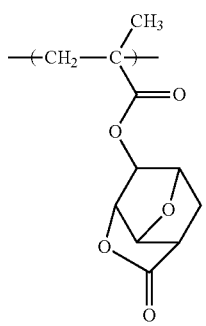 [SMILES: CCC(C)(C)C(=O)OC1C2CC3C(=O)OC1C3O2] B-4

<Preparation of Resist Composition>

Examples 3-1 to 3-10 and Comparative Examples 3-1 to 3-7

The synthesized polymer compound, the following photo acid generator, amine quencher, and alkali-soluble surfactant (F-1) were dissolved in a solvent containing 0.01 mass % of the following surfactant (F-2) (available from Omnova Solutions Inc.) with the composition shown in Table 5. This solution was filtered through a 0.2-μm Teflon (registered trademark) filter to prepare a resist composition (R-01 to R-17).

[Photo Acid Generator]

PAG-A: triphenylsulfonium=2-(adamantane-1-carbonyloxy)-3,3,3-trifluoro-2-trifluoromethylpropane-1-sulfonate (a compound described in Japanese Patent Laid-Open Publication No. 2010-215608)

PAG-B: triphenylsulfonium=2-(adamantane-1-carbonyloxy)-1,1,3,3,3-pentafluoropropane-1-sulfonate (a compound described in Japanese Patent Laid-Open Publication No. 2007-145797)

PAG-C: triphenylsulfonium=2-(adamantane-1-carbonyloxy)ethanesulfonate (a compound described in Japanese Patent Laid-Open Publication No. 2010-155824)

[Organic Solvent]

PGMEA: propylene glycol monomethyl ether acetate

CyHO: cyclohexanone

GBL: γ-butyrolactone

[Amine Quencher]

(Q-1): 2-morpholinoethyl laurate

[Surfactant]

Alkali-soluble surfactant (F-1): poly(3,3,3-trifluoro-2-hydroxy-1,1-dimethyl-2-trifluoromethylpropyl methacrylate/ 1,1,1-trifluoro-2-hydroxy-6-methyl-2-trifluoromethylhepta-4-yl methacrylate) (a compound described in Japanese Patent Laid-Open Publication No. 2008-122932)

Weight average molecular weight (Mw)=7,300

Dispersity (Mw/Mn)=1.86

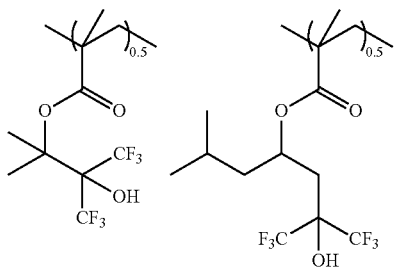

(F-1)

Surfactant (F-2): 3-methyl-3-(2,2,2-trifluoroethoxymethyl)oxetane/tetrahydrofuran/2,2-dimethyl-1,3-propanediol copolymer (available from Omnova Solutions Inc.) Weight average molecular weight (Mw)=1,500

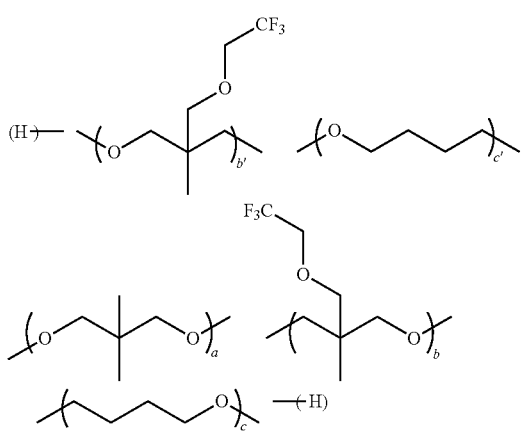

(F-2)

a:(b + b'):(c + c') = 1:4 ~ 7:0.01~1 (mole ratio)

<Resist Composition Evaluation 1 (EUV Exposure)>

Examples 4-1 to 4-6 and Comparative Examples 4-1 to 4-5

For EUV exposure evaluation, the prepared resist composition was applied onto a 4-inch (100-mm) diameter Si substrate subjected to vapor prime treatment with hexamethyldisilazane (HMDS) by spin coating and then pre-baked on a hot plate at 105° C. for 60 seconds to form a resist film with a thickness of 50 nm. The formed resist film was then exposed to EUV by dipole illumination with 0.3 NA. After exposure, heat treatment (PEB) was immediately performed on a hot plate for 60 seconds. Then, puddle development was performed with a 2.38 mass % TMAH aqueous solution for 30 seconds to obtain a positive pattern.

[Evaluation Method]

The obtained resist pattern was evaluated. An exposure dose that allows a 35-nm line and space (LS) pattern of 1:1 was defined as resist sensitivity, and a minimum dimension at this exposure dose was defined as resolution. LWR of the 35-nm LS was measured by a scanning electron microscope (SEM). Table 6 shows the resist compositions, results of sensitivity, resolution, and LWR in the EUV exposure.

TABLE 6

|  | Resist composition | Sensitivity (mJ/cm$^2$) | Resolution (nm) | LWR (nm) |
|---|---|---|---|---|
| Example 4-1 | R-01 | 36 | 35 | 3.4 |
| Example 4-2 | R-02 | 30 | 28 | 3.0 |
| Example 4-3 | R-03 | 25 | 22 | 2.6 |
| Example 4-4 | R-04 | 27 | 24 | 2.8 |
| Example 4-5 | R-05 | 23 | 25 | 3.2 |
| Example 4-6 | R-09 | 32 | 33 | 3.2 |
| Comparative Example 4-1 | R-11 | 20 | 40 | 4.1 |
| Comparative Example 4-2 | R-12 | 40 | 45 | 4.8 |
| Comparative Example 4-3 | R-14 | 25 | 45 | 4.2 |

TABLE 5

|  | Resist composition | Polymer compound (part by mass) | Photo acid generator (part by mass) |  | Amine quencher (part by mass) |  | Surfactant (part by mass) |  | Solvent 1 (part by mass) |  | Solvent 2 (part by mass) |  |
|---|---|---|---|---|---|---|---|---|---|---|---|---|
| Example 3-1 | R-01 | P-1 (80) | — | — | Q-1 | (0.6) | — | — | PGMEA | (576) | CyHO | (1728) |
| Example 3-2 | R-02 | P-2 (80) | — | — | Q-1 | (0.6) | — | — | PGMEA | (576) | CyHO | (1728) |
| Example 3-3 | R-03 | P-3 (80) | — | — | Q-1 | (0.6) | — | — | PGMEA | (576) | CyHO | (1728) |
| Example 3-4 | R-04 | P-4 (80) | — | — | Q-1 | (0.6) | — | — | PGMEA | (576) | CyHO | (1728) |
| Example 3-5 | R-05 | P-5 (80) | — | — | Q-1 | (0.6) | — | — | PGMEA | (576) | CyHO | (1728) |
| Example 3-6 | R-06 | P-6 (80) | — | — | Q-1 | (0.6) | F-1 | (5.0) | PGMEA | (1728) | GBL | (192) |
| Example 3-7 | R-07 | P-7 (80) | — | — | Q-1 | (0.6) | F-1 | (5.0) | PGMEA | (1728) | GBL | (192) |
| Example 3-8 | R-08 | P-8 (80) | — | — | Q-1 | (0.6) | F-1 | (5.0) | PGMEA | (1728) | GBL | (192) |
| Example 3-9 | R-09 | P-1 (80) | PAG-A | (4.0) | Q-1 | (0.6) | — | — | PGMEA | (576) | CyHO | (1728) |
| Example 3-10 | R-10 | P-6 (80) | PAG-B | (3.8) | Q-1 | (0.6) | F-1 | (5.0) | PGMEA | (1728) | GBL | (192) |
| Comparative Example 3-1 | R-11 | P-9 (80) | — | — | Q-1 | (0.6) | — | — | PGMEA | (576) | CyHO | (1728) |
| Comparative Example 3-2 | R-12 | P-10 (80) | — | — | Q-1 | (0.6) | — | — | PGMEA | (576) | CyHO | (1728) |
| Comparative Example 3-3 | R-13 | P-11 (80) | — | — | Q-1 | (0.6) | F-1 | (5.0) | PGMEA | (1728) | GBL | (192) |
| Comparative Example 3-4 | R-14 | P-12 (80) | — | — | Q-1 | (0.6) | — | — | PGMEA | (576) | CyHO | (1728) |
| Comparative Example 3-5 | R-15 | P-13 (80) | PAG-A | (27) | Q-1 | (0.6) | — | — | PGMEA | (576) | CyHO | (1728) |
| Comparative Example 3-6 | R-16 | P-13 (80) | PAG-C | (21) | Q-1 | (0.6) | — | — | PGMEA | (576) | CyHO | (1728) |
| Comparative Example 3-7 | R-17 | P-14 (80) | PAG-B | (13) | Q-1 | (0.6) | F-1 | (5.0) | PGMEA | (1728) | GBL | (192) |

TABLE 6-continued

|  | Resist composition | Sensitivity (mJ/cm$^2$) | Resolution (nm) | LWR (nm) |
|---|---|---|---|---|
| Comparative Example 4-4 | R-15 | 34 | 48 | 4.6 |
| Comparative Example 4-5 | R-16 | 37 | 46 | 4.2 |

The results in Table 6 show that the resist composition containing the inventive polymer compound (Examples 4-1 to 4-6) had good sensitivity, excellent resolution, and small LWR in the EUV exposure.

<Resist Composition Evaluation 2 (ArF Exposure, Evaluation of Hole Pattern by Organic Solvent Development)>

Examples 5-1 to 5-4 and Comparative Examples 5-1 and 5-2

Spin-on carbon film ODL-50 (carbon content: 80 mass %), manufactured by Shin-Etsu Chemical Co., Ltd., was formed on a substrate with a film thickness of 200 nm, and silicon-containing spin-on hard mask SHB-A940 (silicon content: 43 mass %) was formed thereon with a film thickness of 35 nm to obtain a substrate for a tri-layer process. On this substrate, the prepared resist composition was applied by spin coating and baked with a hot plate at 100° C. for 60 seconds to form a resist film with a thickness of 100 nm.

This film was subjected to first exposure with an ArF immersion excimer laser stepper (NSR-610C, manufactured by Nikon Corporation, NA=1.30, σ 0.98/0.78, dipole opening 20°, Azimuthally polarized illumination, 6% halftone phase-shift mask, dipole illumination) using a mask in which lines are arranged in X-direction with 80-nm pitch and 40-nm width in wafer dimension, followed by second exposure using a mask in which lines are arranged in Y-direction with 80-nm pitch and 40-nm width in wafer dimension. After exposure, heat treatment (PEB) was performed for 60 seconds. Then, butyl acetate was discharged through a development nozzle for 3 seconds with a rotation rate of 30 rpm, and static paddle development was performed for 27 seconds to obtain a negative pattern.

[Evaluation Method]

The obtained resist pattern was observed with an electron microscope, and an exposure dose that allows 40-nm hole diameter with 80-nm pitch was defined as optimum exposure dose (sensitivity, mJ/cm$^2$). The result is given in Table 7.

(Evaluation of Critical Dimension Uniformity (CDU))

Hole diameters at different 50 points were observed in one exposure shot with the optimum exposure dose. 3σ variation in dimension was defined as CDU. The result is given in Table 7. The smaller the CDU value is, the better the dimension control is.

(Evaluation of Mask Error Factor (MEF))

A pattern was formed by irradiation with the optimum exposure dose determined in the sensitivity evaluation by using a mask having the same pitch as in the above evaluation using the mask while the line width of the mask was changed. Space widths of the pattern were plotted with the change of the line width of the mask, and a slop of the line thus obtained was calculated as MEF. The more this value approximates to 1, the better the property is. The result is given in Table 7.

(Evaluation of Depth of Focus (DOF) Margin)

The hole dimension at the optimum exposure dose was observed with TDSEM (S-9380) manufactured by Hitachi High-Technologies Corp., to measure DOF with 40 nm±5 nm. The larger this value is, the less the pattern dimension changed with the change of the depth of focus and the better the DOF margin is. The result is given in Table 7.

TABLE 7

|  | Resist composition | Sensitivity (mJ/cm$^2$) | CDU (nm) | MEF (—) | DOF (nm) |
|---|---|---|---|---|---|
| Example 5-1 | R-06 | 35 | 3.2 | 3.1 | 80 |
| Example 5-2 | R-07 | 34 | 3.3 | 3.3 | 80 |
| Example 5-3 | R-08 | 32 | 3.5 | 3.7 | 80 |
| Example 5-4 | R-10 | 28 | 3.5 | 3.5 | 80 |
| Comparative Example 5-1 | R-13 | 30 | 4.6 | 4.0 | 60 |
| Comparative Example 5-2 | R-17 | 36 | 5.0 | 4.2 | 60 |

The results in Table 7 show that the pattern formed by organic solvent development using the inventive resist composition (Examples 5-1 to 5-4) was excellent in CDU, MEF, and DOF margin.

These results demonstrate that the resist composition using the inventive polymer compound as the base resin can form a resist film that has high resolution and high sensitivity and is excellent in balance of lithography properties such as LWR and CDU.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A polymer compound that changes by a high energy beam or heat into a polymer compound having a sulfonic acid structure shown by the formula (1a),

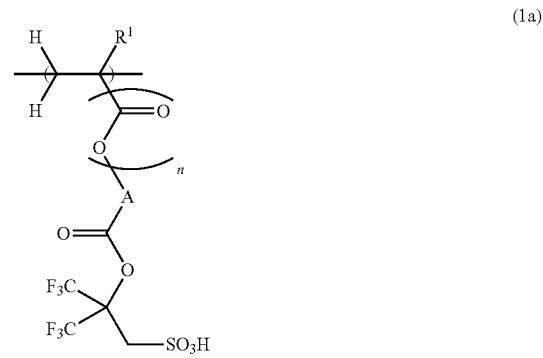

(1a)

wherein R$^1$ represents a hydrogen atom, a fluorine atom, a methyl group, or a trifluoromethyl group; A represents a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; and "n" represents 1;

and further comprising a repeating unit shown by the formula (2) and/or a repeating unit shown by the formula (3),

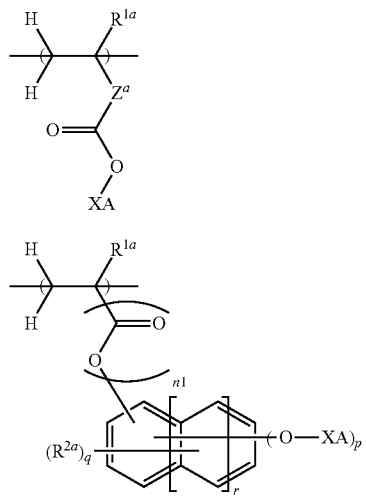

wherein $R^{1a}$ represents a hydrogen atom, a fluorine atom, a methyl group, or a trifluoromethyl group; $Z^a$ represents a single bond or (a main chain) —C(=O)—O—Z'—, where Z' represents a phenylene group, a naphthylene group, or a linear alkylene group having 1 to 10 carbon atoms or a branched or cyclic alkylene group having 3 to 10 carbon atoms, in which the alkylene group may contain a hydroxyl group, an ether bond, an ester bond, or a lactone ring; XA represents an acid-labile group; $R^{2a}$ represents a linear monovalent hydrocarbon group having 1 to 10 carbon atoms or a branched or cyclic monovalent hydrocarbon group having 3 to 10 carbon atoms, in which the hydrocarbon group may contain a heteroatom, and a part or all of hydrogen atoms in the hydrocarbon group may be substituted with a group containing a heteroatom; p represents an integer of 1 to 3; q represents a number satisfying 0<q≤5+2r−p, r represents 0 or 1 and n1 represents 0 or 1.

2. A resist composition comprising (A) the polymer compound according to claim 1 and (B) an organic solvent.

3. A patterning process comprising the steps of: applying the resist composition according to claim 2 on a substrate and baking the resist composition to form a resist film; exposing the formed resist film to a KrF excimer laser beam, an ArF excimer laser beam, an electron beam, or an EUV via a photomask; baking the exposed resist film; and then developing the resist film with a developer.

4. A polymer compound comprising a repeating unit shown by the formula (1c),

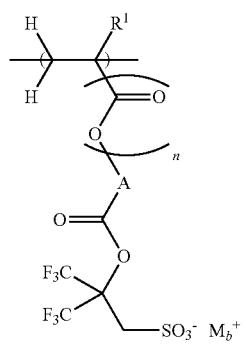

wherein $R^1$ represents a hydrogen atom, a fluorine atom, a methyl group, or a trifluoromethyl group; A represents a linear divalent hydrocarbon group having 1 to 30 carbon atoms or a branched or cyclic divalent hydrocarbon group having 3 to 30 carbon atoms, in which the hydrocarbon group may contain a heteroatom, and a part or all of hydrogen atoms in the hydrocarbon group may be substituted with a group containing a heteroatom; "n" represents 1; and $M_b^+$ represents a sulfonium cation shown by the formula (a) or an iodonium cation shown by the formula (b),

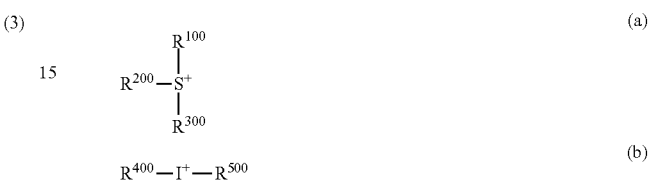

wherein $R^{100}$, $R^{200}$, $R^{300}$, $R^{400}$ and $R^{500}$ independently represent a heteroatom or a linear monovalent hydrocarbon group having 1 to 20 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom; and two or more of $R^{100}$, $R^{200}$, and $R^{300}$ may be bonded to each other to form a ring together with the sulfur atom in the formula; and further comprising a repeating unit shown by the formula (2) and/or a repeating unit shown by the formula (3),

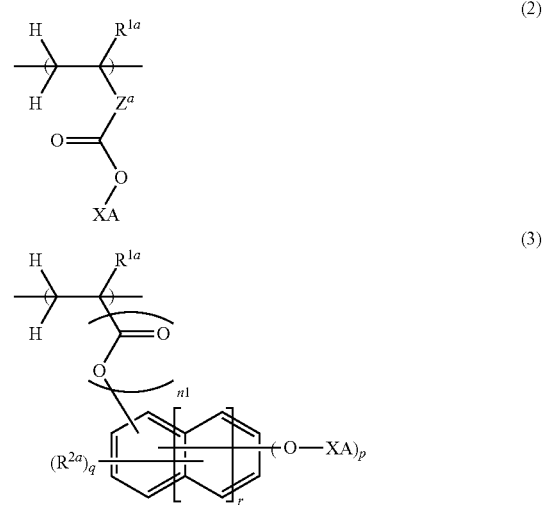

wherein $R^{1a}$ represents a hydrogen atom, a fluorine atom, a methyl group, or a trifluoromethyl group; $Z^a$ represents a single bond or (a main chain) —C(=O)—O—Z'—, where Z' represents a phenylene group, a naphthylene group, or a linear alkylene group having 1 to 10 carbon atoms or a branched or cyclic alkylene group having 3 to 10 carbon atoms, in which the alkylene group may contain a hydroxyl group, an ether bond, an ester bond, or a lactone ring; XA represents an acid-labile group; $R^{2a}$ represents a linear monovalent hydrocarbon group having 1 to 10 carbon atoms or a branched or cyclic monovalent hydrocarbon group having 3 to 10 carbon atoms, in which the hydrocarbon group may contain a heteroatom, and a part or all of hydrogen atoms in the hydrocarbon group may be substituted with a group containing a heteroatom; p represents an integer of 1 to 3; q represents a number satisfying $0<q\leq5+2r-p$, r represents 0 or 1 and n1 represents 0 or 1.

5. A resist composition comprising (A) the polymer compound according to claim 4 and (B) an organic solvent.

6. The resist composition according to claim 5, further comprising (C) a photo acid generator shown by the formula (4),

$$R\text{---}SO_3^- M_b^+ \qquad (4)$$

wherein $M_b^+$ represents a sulfonium cation shown by the formula (a) or an iodonium cation shown by the formula (b); R represents a hydrogen atom or a linear monovalent hydrocarbon group having 1 to 27 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom,

wherein $R^{100}$, $R^{200}$, $R^{300}$, $R^{400}$ and $R^{500}$ independently represent a heteroatom or a linear monovalent hydrocarbon group having 1 to 20 carbon atoms or a branched or cyclic monovalent hydrocarbon group having 3 to 20 carbon atoms, in which the hydrocarbon group may contain a heteroatom, and a part or all of hydrogen atoms in the hydrocarbon group may be substituted with a group containing a heteroatom; and two or more of $R^{100}$, $R^{200}$, and $R^{300}$ may be bonded to each other to form a ring together with the sulfur atom in the formula.

7. The resist composition according to claim 5, further comprising (D) a nitrogen-containing compound.

8. The resist composition according to claim 5, further comprising (E) a surfactant that is insoluble or difficultly soluble in water and soluble in an alkaline developer.

9. A patterning process comprising the steps of: applying the resist composition according to claim 5 on a substrate and baking the resist composition to form a resist film; exposing the formed resist film to a KrF excimer laser beam, an ArF excimer laser beam, an electron beam, or an EUV via a photomask; baking the exposed resist film; and then developing the resist film with a developer.

10. The patterning process according to claim 9, wherein the exposing includes placing a liquid having a refractive index of 1.0 or more between the resist film and a projection lens to perform immersion exposure.

11. The patterning process according to claim 10, wherein the immersion exposure is performed by applying a top coat on the resist film and then placing the liquid having a refractive index of 1.0 or more between the top coat and the projection lens.

* * * * *